(12) United States Patent
Kimura et al.

(10) Patent No.: US 8,513,269 B2
(45) Date of Patent: Aug. 20, 2013

(54) PREPARATION FOR EXTERNAL USE

(75) Inventors: Chiharu Kimura, Kakamigahara (JP); Maho Sakurai, Kakamigahara (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 299 days.

(21) Appl. No.: 12/673,715

(22) PCT Filed: Aug. 15, 2008

(86) PCT No.: PCT/JP2008/064621
§ 371 (c)(1),
(2), (4) Date: Mar. 30, 2010

(87) PCT Pub. No.: WO2009/025239
PCT Pub. Date: Feb. 26, 2009

(65) Prior Publication Data
US 2011/0021545 A1 Jan. 27, 2011

(30) Foreign Application Priority Data
Aug. 17, 2007 (JP) ................. P2007-212926

(51) Int. Cl.
A61K 31/517 (2006.01)
A61P 17/00 (2006.01)

(52) U.S. Cl.
USPC ........................... 514/266.4; 544/292

(58) Field of Classification Search
USPC ..................... 514/266.4; 544/292
See application file for complete search history.

(56) References Cited

U.S. PATENT DOCUMENTS

| | | | |
|---|---|---|---|
| 5,385,907 A | 1/1995 | Asakura et al. | |
| 6,352,989 B1 | 3/2002 | Miyazaki et al. | |
| 6,740,662 B1 | 5/2004 | Iwata et al. | |
| 6,800,644 B2 | 10/2004 | Miyazaki et al. | |
| 2006/0258703 A1 | 11/2006 | Shii et al. | |
| 2007/0299094 A1 | 12/2007 | Miyazaki et al. | |
| 2009/0062539 A1 | 3/2009 | Yamamoto et al. | |

FOREIGN PATENT DOCUMENTS

| | | | |
|---|---|---|---|
| AU | 2007218725 B2 | 8/2007 | |
| JP | 5-17481 A | 1/1993 | |
| JP | 8-165251 A | 6/1996 | |
| JP | 11-209350 A | 8/1999 | |
| JP | 2001-192385 A | 7/2001 | |
| JP | 2001-520196 A | 10/2001 | |
| JP | 2005-29541 A | 2/2005 | |
| JP | 2005-47909 A | 2/2005 | |
| JP | 2005-529930 A | 10/2005 | |
| JP | 2005-537262 A | 12/2005 | |
| JP | 4778550 B2 | 9/2011 | |
| WO | WO-98/10767 A2 | 3/1998 | |
| WO | WO-99/20280 A1 | 4/1999 | |
| WO | WO-99/37622 A1 | 7/1999 | |
| WO | WO-03/099278 A1 | 12/2003 | |
| WO | WO-2004/006920 A1 | 1/2004 | |
| WO | WO-2005/082865 A1 | 9/2005 | |
| WO | WO-2006/093226 A1 | 9/2006 | |
| WO | WO-2007/097317 A1 | 8/2007 | |
| WO | WO-2008/099887 A1 | 8/2008 | |

OTHER PUBLICATIONS

Notice of Allowance in U.S. Appl. No. 12/032,550 issued Feb. 13, 2012.
Office Action dated Feb. 13, 2012 issued in related (not counterpart) Australian patent application No. 2008290000.
Chinese Office Action dated Feb. 15, 2012 issued in related (not counterpart) Chinese patent application No. 200880005202.8.
Office Action dated Feb. 14, 2012 issued in counterpart Australian patent application No. 2008290001.
Office Action dated Mar. 8, 2012 issued in related (not counterpart) Norwegian patent application No. 20083980 (English translation attached).
Australian First Statement of Proposed Amendments dated on Jun. 9, 2010 for Australian Application No. 2008290001.
Canadian Voluntary Amendment dated on Feb. 17, 2010 for Canadian Application No. 2696793.
Chinese Amendment dated on Aug. 13, 2010 for Chinese Application No. 200880022003.8, with English translation.

(Continued)

Primary Examiner — Renee Claytor
Assistant Examiner — Sahar Javanmard
(74) Attorney, Agent, or Firm — Birch, Stewart, Kolasch & Birch, LLP

(57) ABSTRACT

A compound represented by the formula (I), salt thereof, or hydrate thereof has an excellent anti-pruritic effect and an excellent effect in terms of metabolism. The topical formulation of the present invention has excellent skin absorption properties of the compound represented by the formula (I), salt thereof, or hydrate thereof. Furthermore, the topical formulation of the present invention is excellent in stability because ingredients are hardly bled after long-term storage.

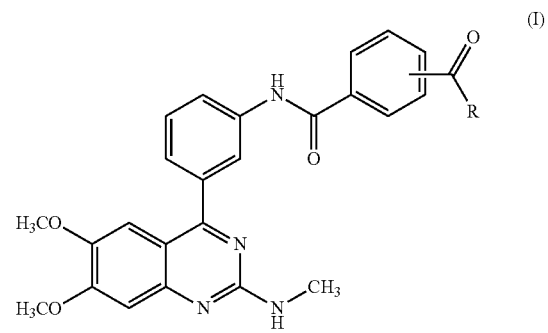

wherein R represents hydroxyl, $C_{1-6}$ alkoxy optionally substituted with $C_{1-6}$ alkoxy, or amino optionally substituted with $C_{1-6}$ alkyl.

7 Claims, 3 Drawing Sheets

(56) References Cited

OTHER PUBLICATIONS

Chinese Notification of the First Office Action dated Sep. 5, 2011 for Chinese Application No. 200880022003.8, with English translation.
Chinese Response to Chinese Office Action dated Nov. 18, 2011 for Chinese Application No. 200880022003.8, with English Translation.
European Amendments Pursuant to Rule 137 EPC dated Mar. 2, 2010 for European Application No. 0882786.6.
European Communication Pursuant to Article 94(3) dated Mar. 17, 2011 for European Application No. 08827867.6.
European Communication Pursuant to Article 94(3) dated Nov. 15, 2010 for European Application No. 08827867.6.
European Communication pursuant to Rules 70(2) and 70a(2) dated Aug. 30, 2010 for European Application No. 08827867.6.
European Communication under Rule 71(3) dated Sep. 5, 2011 for European Application No. 08827867.6.
European Decision to Grant a European Patent Pursuant to Article 97(1) dated Feb. 16, 2012 for European Application No. 08827867.6.
European Reply to Official Communication dated Sep. 20, 2010 for European Application No. 08827867.
European Response to Extended European Search Report dated Sep. 7, 2010 for European Application No. 08827867.6.
European Response to Office Communication dated Apr. 6, 2011 for European Application No. 08827867.6.
European Response to Office Communication dated Jan. 7, 2011 for European Application No. 08827867.6.
Indian Voluntary Amendment filed on Mar. 15, 2010 for Indian Patent Application No. 1457/CHENP/2010.
Israeli Notice of Prior to Examination dated Jun. 5, 2011 for Israeli Patent Application No. 204018, with English translation.
Korean Amendment dated Mar. 18, 2010 for Korean Patent Application No. 10-2009-7026236, with English translation.
Taiwanese Statement of Reasons of Explanation for Voluntary Amendment dated Apr. 27, 2011 for Taiwanese Application No. 097131272, with English translation.
"The Fourth Series of Experimental Chemistry," vol. 1, Fundamental Procedure I, Edited by The Chemical Society of Japan, Maruzen Co. Ltd., 1990, pp. 184-186.
English translations of the Notification of Transmittal of the International Preliminary Report on Patentability (Form PCT/IB/338), International Preliminary Report on Patentability (Form PCT/IB/373), and Written Opinion of the International Searching Authority (Form PCT/ISA/237) issued Aug. 27, 2009, for PCT/JP2008/052448.
Greene et al., "Protective Groups in Organic Synthesis," Third Edition, Protection for the Amino Group, 1999, pp. 518-525, pp. 551-555.
Hanifin et al., Journal of Investigative Dermatology, vol. 107, No. 1, Jul. 1996, pp. 51-56.
Klein et al., Archives of Dermatology, vol. 135, Dec. 1999, pp. 1522-1525.
Leung et al., The Lancet, vol. 361, No. 9352, Jan. 11, 2003, pp. 151-160.
Yosipovitch et al., The Lancet, vol. 361, No. 9358, Feb. 22, 2003, pp. 690-694.
Schmidt, MD et al., "The phosphodiesterase 4 inhibitor roflumilast is effective in the treatment of allergic rhinitis," Journal of Allergy and Clinical Immunology, vol. 108, No. 4, 2001, pp. 530-0536.
English translations of the Notification of Transmittal of the International Preliminary Report on Patentability (Form PCT/IB/338), International Preliminary Report on Patentability (Form PCT/IB/373), Written Opinion of the International Searching Authority (Form PCT/ISA/237) issued Mar. 18, 2010 and International Search Report (Form PCT/ISA/210) issued Sep. 9, 2008 for International Application No. PCT/JP2008/064620.
International Search Report mailed Sep. 9, 2008 in International Application No. PCT/JP2008/064621.
Yakuji Nippo Limited, "Iyakuhin Tenkabutsu Jiten 2007" ("Pharmaceutical Excipients Dictionary 2007"), Edited by Japan Pharmaceutical Excipients Council, Jul. 25, 2007, pp. 280-282 and p. 309.
Notice of Acceptance dated May 1, 2012 issued in related (not counterpart) Australian patent application No. 2008290000.

Response to the Notice Prior to Examination filed on Apr. 22, 2012 for IL Patent Application No. 204018 (English translation attached).
Office Action dated Oct. 5, 2010 for U.S. Appl. No. 11/707,904.
Search Report issued on Aug. 11, 2010 in corresponding European patent application No. 08827867.6.
Yakuji Nippo Limited, "Iyakuhin Tenkabutsu Jiten 2007" ("Pharmaceutical Excipients Dictionary 2007"), Edited by Japan Pharmaceutical Excipients Council, Jul. 25, 2007, pp. 279-280.
International Preliminary Report on Patentability (Forms PCT/IB/338 and PCT/IB/373) and Written Opinion of the International Searching Authority (Form PCT/ISA/237), mailed Mar. 18, 2010, for International Application No. PCT/JP2008/064621.
Japanese Notice of Allowance dated Sep. 25, 2012 issued in related (not counterpart) Japanese Patent Application No. P2008-558123 (With English Translation).
Israeli Notice Prior to Allowance, dated Sep. 19, 2012, for Israeli Application No. 204017, with English translation.
Response (Submission) to Chinese Office Action, dated Sep. 3, 2012, for Chinese Application No. 200880022003.8, with partial English translation.
Norwegian Office Action issued on May 7, 2012, in related (not counterpart) Norwegian patent application No. 20083980 (English translation attached).
Notice of Allowance issued on May 4, 2012, in related (not counterpart) Chinese patent application No. 200880022081.8 (English translation attached).
Chinese Notice of Allowance dated Jun. 6, 2012 issued in related (not counterpart) Chinese Patent Application No. 200880005202.8 (English translation is attached).
Japanese Office Action dated Jun. 26, 2012, for Japanese Application No. 2008-558123.
Australian Office Action dated May 31, 2012 for Australian Patent Application No. 2008215411.
Chinese Office Action dated Jul. 4, 2012 for counterpart Chinese Patent Application No. 200880022003.8, with English translation.
Japanese Decision of Patent Grant dated Jul. 31, 2012 for counterpart Japanese Patent Application No. 2009-529019.
Japanese Notice of Reasons for Rejection dated Jul. 31, 2012 for related (not counterpart) Japanese Patent Application No. 2008-558123.
U.S. Office Action dated Aug. 1, 2012 for U.S. Appl. No. 12/733,169.
Decision of Patent Grant dated Jul. 10, 2012, for Japanese Application No. 2009-529018, including English translation.
Notice of Acceptance dated Jul. 26, 2012, for Australian Application No. 2008290001.
Canadian Notice of Allowance dated Nov. 23, 2012 for CA Patent Application No. 2,637,573, with English translation.
Israeli Office Action dated Oct. 28, 2012 for IL Patent Application No. 193322, with English translation.
Israeli Office Action dated Oct. 28, 2012 for IL Patent Application No. 204018, with English translation.
Korean Office Action dated Nov. 20, 2012 in KR Patent Application No. 10-208-7021869, with English translation.
Norwegian Notice of Allowance dated Nov. 14, 2012 for NO Patent Application No. 20083980, with English translation.
Australian Second Statement of Proposed Amendments dated Jul. 9, 2012 for Australian Application No. 2008290001.
Letter to the Australian Patent Office dated Jul. 9, 2012 for Australian Application No. 2008290001.
Notice of Entitlement dated Apr. 11, 2012 for Australian Application No. 2008290001.
Japanese Office Action issued on May 15, 2012, in counterpart Japanese Patent Application No. 2009-529019 (English translation attached).
Amendment After Allowance for Canadian Application No. 2,637,573, dated Jan. 9, 2013.
Memorandum in Response for Israeli Application No. 204018, dated Jan. 9, 2013.
Notice of Acceptance for Australian Application No. 2008215411, dated Nov. 12, 2012.
Office Action for Taiwan Application No. 097131272, dated Dec. 20, 2012.

Taiwanese Office Action, dated Jan. 3, 2013, for Taiwanese Application No. 096105966, including partial English translation.

US Notice of Allowance, dated Feb. 19, 2013, for U.S. Appl. No. 12/733,169.

Chinese Notice of Allowance dated Jan. 17, 2013 was issued in Chinese Application No. 200880022003.8.

Israeli Memorandum, filed Jan. 6, 2013, in Response to the Office Action dated Oct. 28, 2012, for Israeli Patent Application No. 193322, including English translation.

Korean Argument Brief, dated Dec. 21, 2012, for Korean Patent Application No. 10-2008-7021869, including English translation.

Taiwanese Response to Notification for the Opinion of Examination, filed Mar. 14, 2013, for Taiwanese Patent Application No. 097131272, including English translation.

Canadian Office Action issued in Canadian Application No. 2,678,477 on Apr. 19, 2013, 3 pages.

Canadian Office Action, dated Mar. 21, 2013, for Canadian Application No. 2,696,727.

Korean Notice of Allowance issued in Korean Patent Application No. 10-2008-7021869 on May 20, 2013, 4 pages.

PREPARATION FOR EXTERNAL USE

TECHNICAL FIELD

The present invention relates to a topical formulation comprising a 4-(3-benzoylaminophenyl)-6,7-dimethoxy-2-methylaminoquinazoline compound.

BACKGROUND ART

Phosphodiesterase 4 inhibitor (hereinafter abbreviated as PDE4 inhibitor) is a drug that suppresses the action of the enzyme phosphodiesterase, which degrades cyclic AMP (hereinafter abbreviated as cAMP) and, as a result, has effects of increasing intracellular cAMP concentrations to relax smooth muscle and suppressing activation of inflammatory cells. Therefore, the PDE4 inhibitor is used as a therapeutic agent for bronchial asthma, chronic obstructive pulmonary disease, allergic dermatitis such as atopic dermatitis and contact dermatitis, and the like. Example reports on PDE4 inhibitors are described below. Patent Document 1 discloses that 1,8-naphthyridine derivatives are effective for asthma. Patent Document 2 discloses an eye ointment containing roflumilast. Patent Document 3 discloses a method for treating inflammatory skin disease and allergic skin disease by locally administering a hydroxyindole compound. Patent Document 4 discloses a therapeutic agent for pruritus that contains a piperidine derivative.

A PDE4 inhibitor used for the treatment of an allergic dermatitis is often used as a topical product, which can be directly acted on the skin, in particular, an ointment. In general, an ointment is produced by adding a drug substance and ingredients such as an emulsifier, a solvent, a preservative, a moisturizing agent, and an absorption enhancer to an oily base or a water-soluble base, and mixing these ingredients uniformly. However, some drugs may be hardly absorbed into the skin only by allowing these drugs to exist uniformly in the ointment. In such cases, a method of adding a absorption enhancer to the ointment or suspending or dissolving a drug in a water-soluble or lipid-soluble medium and then kneading the suspension or solution into a base with other additives. For example, Patent Document 5 discloses an ointment produced by dissolving tacrolimus, which is an immunosuppressive agent, in propylene glycol by heating and mixing the solution with paraffin and petrolatum acting as bases, and isopropyl myristate acting as an absorption enhancer. Patent Document 6 discloses an ointment produced by dissolving flurbiprofen or indomethacin, non-steroidal anti-inflammatory agents, in 2-(2-methoxy-1-methylethyl)-5-methylcyclohexanol and mixing the solution with a petrolatum base. Patent Document 7 discloses a water-in-oil ointment produced by dissolving a drug such as azelastine hydrochloride, which is an anti-allergy drug, in propylene glycol and mixing the solution with a white petrolatum base and isopropyl myristate or the like acting as an absorption enhancer.

[Patent Document 1] Japanese Patent Laid-Open No. 2001-192385
[Patent Document 2] National Publication of International Patent Application No. 2005-529930
[Patent Document 3] National Publication of International Patent Application No. 2005-537262
[Patent Document 4] Japanese Patent Laid-Open No. 2005-47909
[Patent Document 5] Japanese Patent Laid-Open No. 5-17481
[Patent Document 6] Japanese Patent Laid-Open No. 8-165251
[Patent Document 7] Japanese Patent Laid-Open No. 2005-29541
[Patent Document 8] WO99/37622

DISCLOSURE OF THE INVENTION

Problems to be Solved by the Invention

Some PDE4 inhibitors have a defect that they are poorly absorbed into the skin when used as a topical product. Therefore, to improve the absorption property, it may occasionally be necessary to contain a liquid ingredient such as a large quantity of solvent for dissolving the compound or an absorption enhancer in the formulation. However, this may cause phase separation and bleeding of the liquid components from the formulation. Accordingly, the objective of this invention is to provide a topical formulation which allows high absorption of PDE4 inhibitor and does not result in bleeding of the component.

As a result of intensive studies, the present inventors have found that a novel compound represented by the formula (I), salt thereof, or hydrate thereof is a PDE4 inhibitor that has an excellent anti-pruritic effect.

[Formula 1]

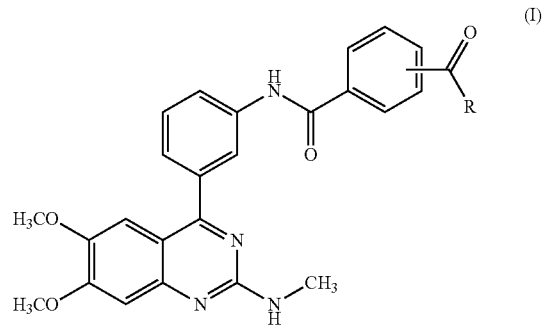

wherein R represents hydroxyl, $C_{1-6}$ alkoxy optionally substituted with $C_{1-6}$ alkoxy, or amino optionally substituted with $C_{1-6}$ alkyl.

The following compound is disclosed in Patent Document 8 as an example of compounds that are similar to the compound represented by the formula (I) in structure.

[Formula 2]

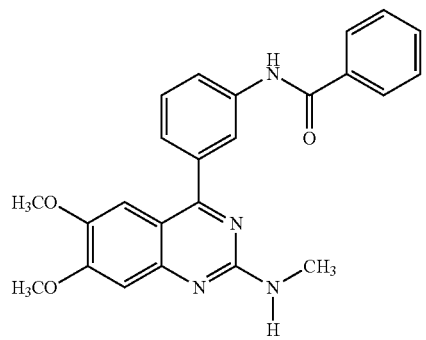

It is described in Patent Document 8, that this compound has PDE4 inhibitory action and thereby has anti-inflammatory action based on the PDE4 inhibitory action. Although Patent Document 8 describes that the above compound is effective for the treatment of psoriasis based on the anti-inflammatory action, the above publication neither describes nor suggests application of the above compound to itch caused by atopic disease. Furthermore, Patent Document 8 neither describes nor suggests that the compound described in Patent Document 8 is effective for itch on which a steroid drug or an anti-histamine agent is not effective. In contrast, the present inventors have found that the compound represented by the formula (I), or salt thereof, or hydrate thereof has an excellent anti-pruritic effect and is effective for itch caused by atopic disease or the like.

Furthermore, the present inventors have found that the compound represented by the formula (I), or salt thereof or hydrate thereof has insufficient skin absorption properties when used as a topical formulation. Accordingly, as a result of further studies, the present inventors could developed the formulation that the absorption properties of the compound represented by the formula (I), salt thereof, or hydrate thereof can be improved, and the bleeding of the components from the formulation can be prevented, and then accomplished the present invention.

Means for Solving the Problems

That is to say, the present invention provides the following [1] to [15]:
[1] a topical formulation, comprising a compound represented by the formula (I), salt thereof, or hydrate thereof, a solvent, and a base:

[Formula 3]

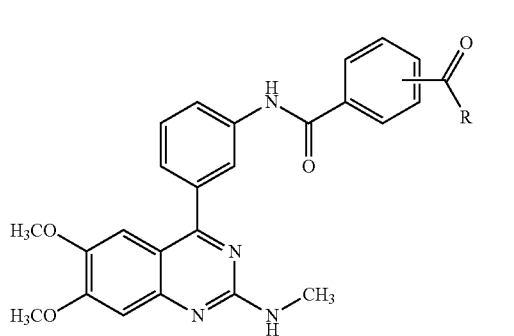

(I)

wherein R represents hydroxyl, $C_{1-6}$ alkoxy optionally substituted with $C_{1-6}$ alkoxy, or amino optionally substituted with $C_{1-6}$ alkyl.
[2] the topical formulation according to [1], wherein the compound represented by the formula (I) is methyl N-[3-(6,7-dimethoxy-2-methylaminoquinazolin-4-yl)phenyl]terephthalamic acid.
[3] the topical formulation according to [1] or [2], comprising an absorption enhancer.
[4] the topical formulation according to any one of [1] to [3], comprising a bleeding preventing agent.
[5] the topical formulation according to [4], comprising two or more types of bleeding preventing agents.
[6] the topical formulation according to any one of [1] to [5], comprising water.
[7] the topical formulation according to any one of [1] to [6], wherein the base is one or more types selected from the group consisting of petrolatum, paraffin, liquid paraffin, microcrystalline wax, carunauba wax, and white beeswax.
[8] the topical formulation according to any one of [1] to [7], wherein the solvent is one or more types selected from the group consisting of polyethylene glycol having a molecular weight of 200 to 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, and oleic acid.
[9] the topical formulation according to any one of [3] to [8], wherein the absorption enhancer is one or more types selected from the group consisting of isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, and diethyl phthalate.
[10] the topical formulation according to any one of [4] to [9], wherein the bleeding preventing agent is one or more types selected from the group consisting of polyethylene glycol having a molecular weight of 1000 to 50000, polyoxyethylene hydrogenated castor oil, stearic acid, oleic acid, sorbitan monostearate, sorbitan monooleate, sorbitan sesquioleate, sorbitan trioleate, and glycerol esters of fatty acids.
[11] the topical formulation according to [10], wherein the glycerol esters of fatty acids is one or more types selected from the group consisting of glyceryl monostearate, diglyceryl isostearate, and hexaglyceryl polyricinoleate.
[12] the topical formulation according to [10], wherein the bleeding preventing agent is polyethylene glycol having a molecular weight of 1000 to 50000 and glycerol esters of fatty acids.
[13] the topical formulation according to [11], wherein the glycerol esters of fatty acids is glyceryl monostearate.
[14] the topical formulation according to any one of [3] to [13], wherein the topical formulation comprises 10 to 30% by weight of a solvent and 5 to 20% by weight of an absorption enhancer, and the sum of the solvent and absorption enhancer is 20 to 40% by weight based on the total preparation amount, respectively.
[15] a method for preventing bleeding of liquid ingredients, comprising mixing polyethylene glycol having a molecular weight of 1000 to 50000 and glycerol esters of fatty acids in a topical formulation according to [1] to [14].

Effect of the Invention

The compound represented by the formula (I), salt thereof, or hydrate thereof of the present invention has an excellent anti-pruritic effect as well as an excellent effect in terms of metabolism. Furthermore, the topical formulation of the present invention has excellent skin absorption properties of the compound represented by the formula (I), salt thereof, or hydrate thereof. Furthermore, the topical formulation of the present invention has excellent stability because it can prevent the bleeding (the separation of the ingredients) the component from the formulation after storage over a long period of time.

BEST MODE FOR CARRYING OUT THE INVENTION

Figure 1:
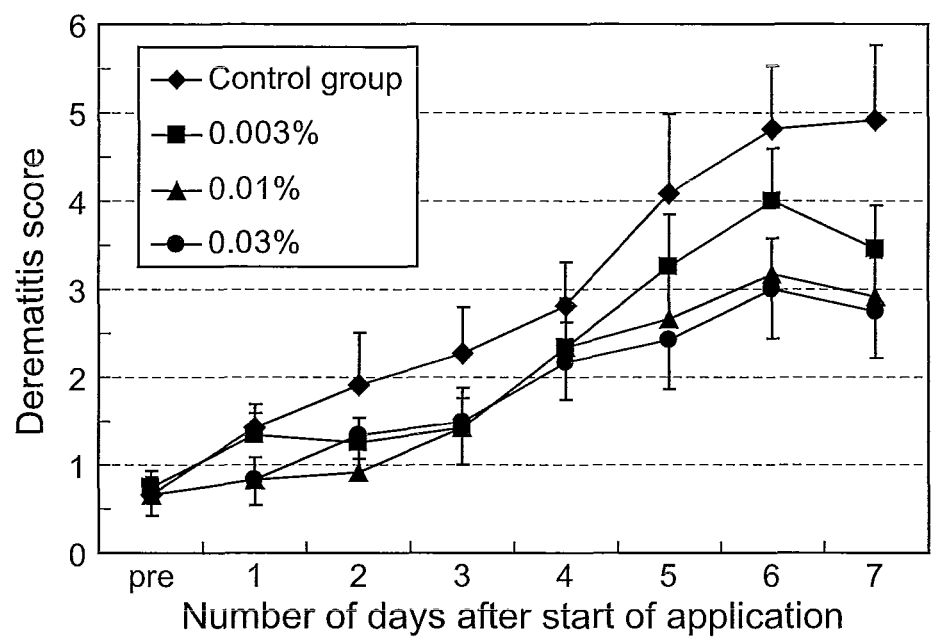
FIG. 1 shows that dermatitis is suppressed by the ointment of the present invention.

The present invention will be described in detail below.

In the present specification, the structural formula of a compound may indicate a certain type of isomer, as a matter of convenience. The present invention includes all isomers generated because of the structure of a compound, such as a geometric isomer, an optical isomer, a stereoisomer, or a tautomer, and an isomeric mixture. Thus, the compound of the present invention is not limited to the descriptions of a formula provided as a matter of convenience, but it may be either one of such isomers or a mixture thereof. Accordingly, an optically active form and a racemic form may exist in the compound of the present invention. In the present invention, such an optically active form and a racemic form are not limited, and any of them are included. In addition, a crystal polymorphism may also exist in the compound of the present invention. Such a crystal polymorphism is not limited either, and the present invention may be either a single crystal form or a mixture thereof. Moreover, the present invention also includes an amorphous form, and the compound of the present invention includes an anhydrate and a hydrate. Furthermore, the present invention also includes so-called a metabolite, which is generated as a result of in vivo metabolism (oxidation, reduction, hydrolysis, conjugation, etc.) of the compound (I) of the present invention. Still further, a compound (so-called a prodrug), which generates the compound (I) of the present invention as a result of in vivo metabolism (oxidation, reduction, hydrolysis, conjugation, etc.), is also included in the present invention.

The definitions of terms, symbols, and others used in the present specification will be explained below, and the present invention will be described in detail below.

The term "$C_{1-6}$ alkyl" is used in the present specification to mean a linear or branched-chain alkyl group containing 1 to 6 carbon atoms. Specific examples of $C_{1-6}$ alkyl may include methyl, ethyl, 1-propyl (n-propyl), 2-propyl (i-propyl), 2-methyl-1-propyl (i-butyl), 2-methyl-2-propyl (t-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2,-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, and 2,3-dimethyl-2-butyl.

Preferred examples may include $C_{1-3}$ alkyl such as methyl, ethyl, 1-propyl (n-propyl), 2-propyl (i-propyl), 2-methyl-1-propyl (i-butyl), 2-methyl-2-propyl (t-butyl), 1-butyl (n-butyl), or 2-butyl (s-butyl). More preferred examples may include methyl and ethyl.

The term "$C_{1-6}$ alkoxy" is used in the present specification to mean an oxy group to which the above defined "$C_{1-6}$ alkyl" binds. Specific examples of $C_{1-6}$ alkoxy may include methoxy, ethoxy, 1-propoxy, 2-propoxy, 2-methyl-1-propoxy, 2-methyl-2-propoxy, 1-butoxy, 2-butoxy, 1-pentoxy, 2-pentyloxy, 3-pentyloxy, 2-methyl-1-butoxy, 3-methyl-1-butoxy, 2-methyl-2-butoxy, 3-methyl-2-butoxy, 2,2-dimethyl-1-propoxy, 1-hexyloxy, 2-hexyloxy, 3-hexyloxy, 2-methyl-1-pentoxy, 3-methyl-1-pentyloxy, 4-methyl-1-pentoxy, 2-methyl-2-pentoxy, 3-methyl-2-pentoxy, 4-methyl-2-pentoxy, 2-methyl-3-pentyloxy, 3-methyl-3-pentyloxy, 2,3-dimethyl-1-butoxy, 3,3-dimethyl-1-butoxy, 2,2-dimethyl-1-butoxy, 2-ethyl-1-butoxy, 3,3-dimethyl-2-butoxy, 2,3-dimethyl-2-butoxy and the like.

Preferred examples may include $C_{1-3}$ alkoxy such as methoxy, ethoxy, 1-propoxy, and 2-propoxy. A more preferred example is methoxy.

In addition, examples of "$C_{1-6}$ alkoxy optionally substituted with $C_{1-6}$ alkoxy" in the definitions of R may include methoxymethoxy, ethoxymethoxy, methoxyethoxy, and ethoxyethoxy.

Examples of "amino optionally substituted with $C_{1-6}$ alkyl" in the present specification may include amino, mono-$C_{1-6}$ alkylamino that is substituted with the aforementioned $C_{1-6}$ alkyl (for example, methylamino, ethylamino, t-butylamino, etc.), di-$C_{1-6}$ alkylamino (for example, dimethylamino, diethylamino, methylethylamino, etc.) and the like.

Preferred examples may include amino, mono-$C_{1-3}$ alkylamino, and di-$C_{1-3}$ alkylamino. More preferred examples may include amino and monomethylamino.

The type of a "salt" used in the present specification is not particularly limited, as long as it forms a salt together with the compound of the present invention and it is pharmacologically acceptable. Examples of such a salt may include an inorganic acid salt, an organic acid salt, an inorganic basic salt, an organic basic salt, an acidic or basic amino acid salt and the like.

Preferred examples of an inorganic acid salt may include hydrochloride, hydrobromide, sulfate, nitrate, phosphate and the like. More preferred examples are hydrochloride, hydrobromide, sulfate, and phosphate. Preferred examples of an organic acid salt may include acetate, succinate, fumarate, maleate, tartrate, citrate, lactate, stearate, benzoate, methanesulfonate, ethanesulfonate, p-toluenesulfonate, and benzenesulfonate and more preferred examples are methanesulfonate or p-toluenesulfonate.

Preferred examples of an inorganic basic salt may include: alkaline metal salts such as a sodium salt or a potassium salt; alkaline-earth metal salts such as a calcium salt or a magnesium salt; aluminum salts; ammonium salts and the like. Preferred examples of an organic basic salt may include a diethylamine salt, a diethanolamine salt, a meglumine salt, an N,N'-dibenzylethylenediamine salt and the like.

Preferred examples of an acidic amino acid salt may include aspartate and glutamate. Preferred examples of a basic amino acid salt may include an arginine salt, a lysine salt, an ornithine salt and the like.

The topical formulation according to the present invention means an ointment preparation, a gel preparation, a cream preparation, a patch preparation, an eye ointment preparation, a suppository preparation and the like and preferably an ointment preparation.

The active ingredient in the topical formulation according to the present invention is a compound represented by the formula (I), salt thereof, or hydrate thereof:

[Formula 4]

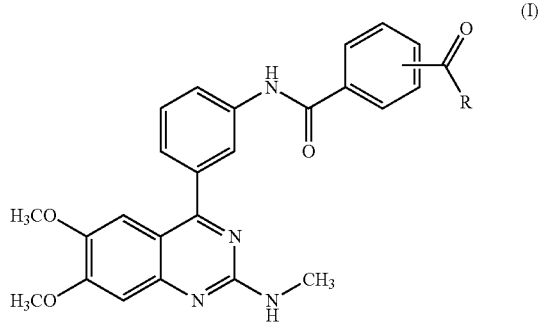

wherein R represents hydroxyl, $C_{1-6}$ alkoxy optionally substituted with $C_{1-6}$ alkoxy, or amino optionally substituted with $C_{1-6}$ alkyl.

Examples of the compound represented by the formula (I) include:
methyl N-[3-(6,7-dimethoxy-2-methylaminoquinazolin-4-yl)phenyl]terephthalamic acid;
N-[3-(6,7-dimethoxy-2-methylaminoquinazolin-4-yl)phenyl]terephthalamic acid hydrochloride;
N-[3-(6,7-dimethoxy-2-methylaminoquinazolin-4-yl)phenyl]-N',N'-dimethylterephthalamide;
ethyl N-[3-(6,7-dimethoxy-2-methylaminoquinazolin-4-yl)phenyl]terephthalamic acid;
N-[3-(6,7-dimethoxy-2-methylaminoquinazolin-4-yl)phenyl]-N'-methylterephthalamide;
propyl N-[3-(6,7-dimethoxy-2-methylaminoquinazolin-4-yl)phenyl]terephthalamic acid;
isopropyl N-[3-(6,7-dimethoxy-2-methylaminoquinazolin-4-yl)phenyl]terephthalamic acid;
N-[3-(6,7-dimethoxy-2-methylaminoquinazolin-4-yl]-N'-ethylterephthalamide;
N-[3-(6,7-dimethoxy-2-methylaminoquinazolin-4-yl)phenyl]-N'-propylterephthalamide;
N-[3-(6,7-dimethoxy-2-methylaminoquinazolin-4-yl)phenyl]-N'-isopropylterephthalamide;
methyl N-[3-(6,7-dimethoxy-2-methylaminoquinazolin-4-yl)phenyl]isophthalic acid;
N-[3-(6,7-dimethoxy-2-methylaminoquinazolin-4-yl)phenyl]isophthalic acid;
ethyl N-[3-(6,7-dimethoxy-2-methylaminoquinazolin-4-yl)phenyl]isophthalic acid;
propyl N-[3-(6,7-dimethoxy-2-methylaminoquinazolin-4-yl)phenyl]isophthalic acid;
isopropyl N-[3-(6,7-dimethoxy-2-methylaminoquinazolin-4-yl)phenyl]isophthalic acid;
N-[3-(6,7-dimethoxy-2-methylaminoquinazolin-4-yl)phenyl]-N'-methylisophthalamide;
N-[3-(6,7-dimethoxy-2-methylaminoquinazolin-4-yl)phenyl]-N'-ethylisophthalamide;
N-[3-(6,7-dimethoxy-2-methylaminoquinazolin-4-yl)phenyl]-N'-propylisophthalamide
N-[3-(6,7-dimethoxy-2-methylaminoquinazolin-4-yl)phenyl]-N'-isopropylisophthalamide;
N-[3-(6,7-dimethoxy-2-methylaminoquinazolin-4-yl)phenyl]terephthalamic acid 2-methoxyethyl ester; and
N-[3-(6,7-dimethoxy-2-methylaminoquinazolin-4-yl)phenyl]isophthalamic acid 2-methoxyethyl ester.

Preferably, the compound represented by the formula (I) is methyl N-[3-(6,7-dimethoxy-2-methylaminoquinazolin-4-yl)phenyl]terephthalamic acid.

The compound represented by the formula (I) can be produced, for example, by the method described below.

[Formula 5]

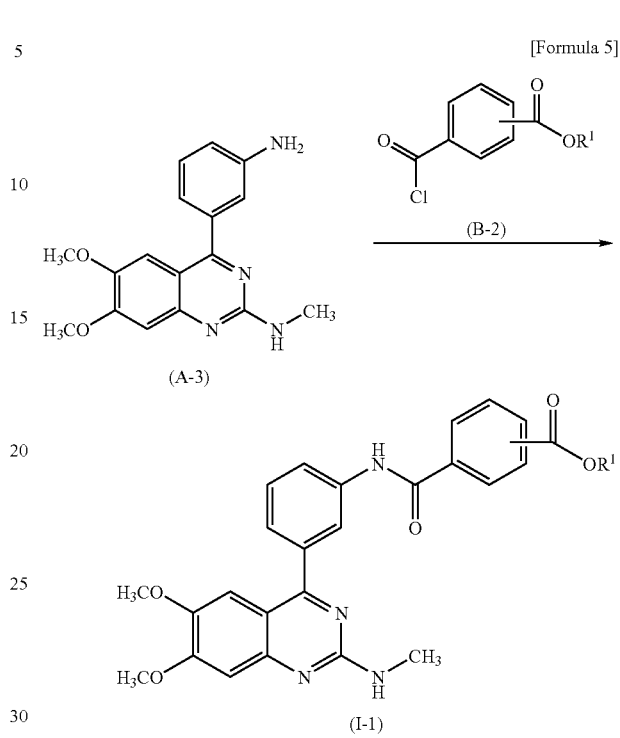

[wherein $R^1$ represents $C_{1-6}$ alkyl.]

This is a method of allowing a compound (A-3) to react with a compound (B-2) that is acid chloride in an inert solvent in the presence or absence of a base, so as to produce the compound (I-1) of the present invention.

A compound (A-3) can be produced by production example 7 in WO 99/37622.

As such a compound (B-2), a known compound, a commercially available compound, or a compound that can easily be produced from a commercially available compound by a method that is generally carried out by those skilled in the art, can be used. Examples of such a compound (B-2) may include 4-chlorocarbonyl benzoic acid methyl ester and the like.

The compound (B-2) can be used in an amount of 1 to 10 times, and preferably 1 to 2 times the molar equivalent of the compound (A-3).

The type of a solvent used is not particularly limited, as long as it dissolves starting substances to a certain extent and it does not inhibit the reaction in the present step. Examples of a solvent may include: aromatic hydrocarbons such as toluene, benzene, xylene and the like; ethers such as diethyl ether, tetrahydrofuran, dimethoxyethane, dioxane and the like; halogenated hydrocarbons such as dichloromethane, chloroform, 1,2-dichloroethane, or carbon tetrachloride; organic bases such as pyridine, 2-, 3- or 4-picoline and the like; water; and a mixture of these solvents. Preferred examples are tetrahydrofuran or pyridine.

The type of a base used herein is not particularly limited, as long as a compound of interest can be obtained and non-separable by-products are not generated. Examples of a base may include: inorganic bases such as sodium carbonate, potassium carbonate, sodium hydrogencarbonate, potassium hydrogencarbonate, cesium carbonate and the like; and organic bases such as pyridine, triethylamine and the like. A preferred example is pyridine.

The aforementioned base can be used in an amount of 1 to 10 times, and preferably 1 to 4 times the molar equivalent of the compound (A-3).

The reaction temperature depends on a solvent and a reagent used. It is generally between −30° C. and 180° C., and preferably between 0° C. and 100° C.

The reaction time depends on a solvent used and the reaction temperature. It is generally between 0.5 and 200 hours, and preferably between 1 and 100 hours.

The compound represented by the formula (I) can be obtained by hydrolyzing and esterifying or amidating the compound (I-1) if necessary. When the compound represented by the formula (I) is obtained in a free form, such a free form can be converted to a salt or hydrate according to common methods. Furthermore, when the compound represented by the formula (I) is obtained in a form of a salt or hydrate, these compounds can be converted to a free form according to common methods.

The topical formulation of the present invention comprises a solvent and a base in addition to the aforementioned active ingredient. The present inventors have found that, when a topical product is formulated by mixing an active ingredient and a base, skin absorption properties may become insufficient. The skin absorbability of the active ingredient in the topical formulation of the present invention is improved by adding a solvent.

A solvent commonly used for a topical formulation can be used as the solvent, and specific examples may include polyethylene glycol having a molecular weight of 200 to 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, and oleic acid. A preferred example of the solvent is polyethylene glycol having a molecular weight of 200 to 600.

Polyethylene glycol having a molecular weight of 200 to 600 means polyethylene glycol having an average molecular weight of 200 to 600 as a result of average molecular weight testing directed in the section of macrogol 400 in The Japanese Pharmacopoeia Fifteenth Edition. Among polyethylene glycols having a molecular weight 200 to 600, polyethylene glycols 400 having an average molecular weight of 380 to 420 as a result of average molecular weight testing directed in the section of macrogol 400 in The Japanese Pharmacopoeia Fifteenth Edition are particularly preferred.

A base commonly used as a base of a topical formulation, in particular, an oleaginous base, can be used, and specific examples may include petrolatum, squalane, paraffin, liquid paraffin, microcrystalline wax, carunuba wax, white beeswax and the like. A preferred example of the base is petrolatum, and a particularly preferred example of the base is white petrolatum.

The topical formulation of the present invention may further comprise an absorption enhancer and/or bleeding preventing agent. The skin absorbability of the active ingredient can be further improved by adding an absorption enhancer. Furthermore, the bleeding of ingredients (in particular, a solvent and absorption enhancer) from the topical formulation of the present invention can be prevented by adding a bleeding preventing agent, and thus stability can be achieved.

An absorption enhancer commonly used as an absorption enhancer of a topical formulation can be used, and specific examples may include isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, diethyl phthalate and the like. A preferred example of the absorption enhancer is isopropyl myristate.

A bleeding preventing agent commonly used as a bleeding preventing agent of a topical formulation can be used, and specific examples may include polyethylene glycol having a molecular weight of 1000 to 50000, polyoxyethylene hydrogenated castor oil, stearic acid, oleic acid, sorbitan monostearate, sorbitan monooleate, sorbitan sesquioleate, sorbitan trioleate, glycerol esters of fatty acids and the like. Examples of the glycerol esters of fatty acids may include glyceryl monostearate, diglyceryl isostearate, hexaglyceryl polyricinoleate and the like, and a preferred example is glyceryl monostearate.

It is preferable to use two or more types of bleeding preventing agents because the bleeding preventing effect can be increased. Preferred bleeding preventing agents are a combination of polyethylene glycol having a molecular weight of 1000 to 50000 and glyceryl monostearate. Bleeding of a solvent, in particular, polyethylene glycol having a molecular weight of 200 to 600 can be prevented by using polyethylene glycol having a molecular weight of 1000 to 50000. Furthermore, bleeding of an absorption enhancer, in particular, isopropyl myristate can be prevented by using glyceryl monostearate.

The polyethylene glycol having a molecular weight 1000 to 50000 means polyethylene glycol having an average molecular weight of 1000 to 50000 as a result of average molecular weight testing directed in the section of macrogol 4000 in The Japanese Pharmacopoeia Fifteenth Edition. Among polyethylene glycols having a molecular weight of 1000 to 50000, polyethylene glycols 4000 having an average molecular weight of 2600 to 3800 as a result of average molecular weight testing directed in the section of macrogol 4000 in The Japanese Pharmacopoeia Fifteenth Edition are particularly preferred.

The topical formulation of the present invention may further comprise water. Degradation of an active ingredient can be suppressed by adding water.

The topical formulation of the present invention may comprise a coloring agent, a flavoring agent, a preservative, an antioxidant, a stabilizer, a usability improving agent and the like other than the above ingredients.

The coloring agent may include iron sesquioxide, yellow iron sesquioxide, carmine, caramel, beta-carotene, titanium oxide, talc, riboflavin sodium phosphate, yellow aluminum lake, and the like.

The flavoring agent may include cocoa powder, mentha oil, menthol, lemon oil, borneol, powdered cinnamon bark, ascorbic acid, citric acid, tartaric acid, malic acid, aspartame, potassium acesulfame, and the like The preservative may include methylparaben, propylparaben, chlorobutanol, benzyl alcohol, phenethyl alcohol, dehydroacetic acid, sorbic acid and the like.

The antioxidant may include sulfite salts, ascorbic acid, tocopherol and the like.

The stabilizer may include ascorbic acid, edetic acid salt, erythorbic acid, tocopherol and the like.

The usability improving agent may include polyoxyethylene hydrogenated castor oil 40, polyoxyethylene hydrogenated castor oil 60 and the like.

The amounts of ingredients in the topical formulation of the present invention can be suitably set, as long as the effect of the present invention is not impaired, but are preferably within the following ranges (expressed with % by weight based on the total amount of the formulation): active ingredient, 0.001 to 0.5% by weight; solvent, 10 to 30% by weight; base, 40 to 70% by weight; absorption enhancer, 5 to 20% by weight; bleeding preventing agent, 10 to 25% by weight; and water, 0.1 to 5%. Here, the total amount of a solvent and an absorption enhancer is preferably 20 to 40% by weight. Furthermore, the amount of water mixed is preferably 0.3 to 3%, more preferably 0.5 to 2%.

The topical formulation of the present invention can be manufactured according to common manufacturing methods for a topical formulation. Such a method will be described below using an ointment as an example. First, the compound represented by the formula (I), salt thereof, or hydrate thereof, which is an active ingredient, is dissolved in a solvent by heating at 70° C. to 80° C. (Solution I). Meanwhile, an absorption enhancer and a bleeding preventing agent and other ingredients are added to the base if necessary and are dissolved by heating at 70° C. to 80° C. And then, solution I and water if necessary are added to the resulting mixture, and the mixture is stirred at 70° C. to 80° C. for approximately 3 minutes. The mixing is maintained until the mixture was cooled down to approximately 32° C. (around the human skin surface temperature) and an ointment is completed. An antioxidizing agent may be added to the solvent if necessary.

EXAMPLES

The compound represented by the formula (I), salt thereof, or hydrate thereof can be produced by the methods described in the following production examples. However, these examples are provided for illustrative purposes only. Specific examples as described below are not intended to limit the scope of the invention in any case. In addition, various modifications may also be made within the scope of the present invention. Compounds, to which publication names or the like are attached, were produced in accordance with the publications or the like.

Production Example A

Synthesis of 3-(2-chloro-6,7-dimethoxy-quinazolin-4-yl)phenylamine

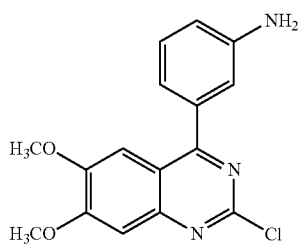

[Formula 6]

Twenty-five grams of 2,4-dichloro-6,7-dimethoxyquinazoline was suspended in 2.25 L of a mixed solution consisting of toluene:tetrahydrofuran:a 2 N sodium carbonate solution=1:1:1. To the reaction mixture was added 21.5 g of 3-aminophenyl boronic acid ½ sulfate, and the mixture was degassed, the atmosphere in the reaction vessel was replaced with nitrogen. To the reaction mixture was added 2.23 g of tetrakis(triphenylphosphine)palladium(0), followed by stirring at 60° C. under a nitrogen atmosphere. Eighteen hours after initiation of the reaction, 1.2 g of tetrakis(triphenylphosphine)palladium(0) was added to the reaction mixture, and the stirring was continued. Thirty hours later, 1.2 g of tetrakis(triphenylphosphine)palladium(0) was further added to the reaction mixture, and stirring was further continued. Forty-eight hours after initiation of the reaction, the reaction mixture was cooled, and it was then transferred into a separatory funnel, so as to separate an organic layer. The obtained organic layer was washed with 300 mL of brine, and was then dried over anhydrous magnesium sulfate. The desiccant was removed by passing it through 250 g of silica gel. The silica gel was washed with 1.5 L of ethyl acetate, and the obtained organic layers were combined and concentrated to dryness. The residue was triturated with 200 mL of ethyl acetate, and the obtained solid was then filtrated. The solid was washed with 100 mL of diethyl ether and 200 mL of a mixed solution consisting of n-heptane:ethyl acetate=1:1, and dried under aeration to give 28.2 g of a target product. Yield: 92.5%

$^1$H-NMR (DMSO-$d_6$) δ (ppm): 3.86 (3H, s), 4.01 (3H, s), 5.40 (2H, br), 6.79 (1H, dd, J=1.6, 8.0 Hz), 6.93 (1H, brd, J=8.0 Hz), 7.02 (1H, t, J=1.6 Hz), 7.24 (1H, t, J=8.0 Hz), 7.41 (1H, s), 7.43 (1H, s).

Production Example B

Synthesis of [4-(3-aminophenyl)-6,7-dimethoxyquinazolin-2-yl]methylamine

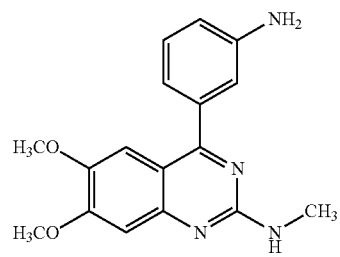

[Formula 7]

Fourteen grams of 3-(2-chloro-6,7-dimethoxyquinazolin-4-yl)phenylamine was suspended in 135 mL of a mixed solution consisting of tetrahydrofuran:isopropanol=2:1. To the reaction mixture was added 89 mL of a methylamine solution in methanol, and the reaction mixture was stirred in a pressure-resistant sealed tube reactor at 130° C. for 24 hours. After the reaction mixture was allowed to cool down to room temperature, it was diluted with 300 mL of ethyl acetate and then washed with 300 mL of water. A water layer was extracted with 100 mL of ethyl acetate, and the combined organic layer was washed with 100 mL of brine. The organic layer was separated and was then dried over anhydrous magnesium sulfate. The desiccant was removed by filtration, the organic layer was concentrated to dryness, and the resultant was triturated with a mixed solvent consisting of ethyl acetate:tetrahydrofuran=3:1. The obtained solid was filtrated, and the filtrate was then washed with ethyl acetate, and dried under aeration to yield 10 g of a product of interest. The filtrate was adsorbed on a 50 g silica gel column, and it was then eluted with a mixed solution consisting of ethyl acetate:methanol=9:1, and the eluent was concentrated to dryness. The residue was triturated with ethyl acetate, and the obtained solid was then filtrated. The solid was washed with diethyl ether, and dried under aeration to give 1.4 g of a target product. Total yield: 82.9%

$^1$H-NMR (CDCl$_3$) δ (ppm): 3.12 (3H, d, J=5.2 Hz), 3.80 (2H, brs), 3.82 (3H, s), 4.03 (3H, s), 5.30 (1H, br), 6.83 (1H, dd, J=1.6, 8.0 Hz), 6.99 (1H, t, J=1.6 Hz), 7.04 (1H, brd, J=8.0 Hz), 7.07 (1H, s), 7.15 (1H, s), 7.30 (1H, t, J=8.0 Hz).

Production Example C

Alternative Method for Synthesis of 3-(2-chloro-6,7-dimethoxy-quinazolin-4-yl)phenylamine (Production example A)

To 634 g of sodium carbonate (5.98 mol) was added 2.91 kg of water under a nitrogen atmosphere, followed by stirring for dissolution. To the solution were added 3.0 L of tetrahydrofuran, 431 g of 3-aminophenyl boronic acid monohydrate (2.78 mol), 30.4 g of triphenylphosphine (0.116 mol) and 26.0 g of dichloropalladium (0.116 mol) in this order. To the mixture was dropwise added a solution of 2,4-dichloro-6,7-dimethoxyquinazoline (600 g; 2.32 mol) in tetrahydrofuran (12.0 L) over 2 hours while stirring at 60° C., followed by stirring at the same temperature for 16 hours. To the mixture were added 3.0 kg of a 5% sodium chloride solution and 12.0 L of tetrahydrofuran in this order, and the mixture was stirred at 50° C. for 1 hour and allowed to cool down to 25° C. The mixture was filtered through celite to remove the insoluble matter, and the filtrate was transferred to separatory funnel and the organic layer was separated. To the separated organic layer were added 150 g of anhydrous magnesium sulfate and 60.0 g of activated carbon, and the mixture was stirred at 50° C. for 1 hour and allowed to cool down to 25° C. The mixture was filtered through celite to remove the insoluble matter, and the filtrate was concentrated under reduced pressure. To the residue was added 6.0 L of water, and the mixture was stirred at room temperature for 1 hour, and precipitated crystals were collected by filtration. The collected crystals were dried at 50° C. under reduced pressure to give 730 g (content rate 62.2%) of a target product. Yield: 62.1%

Production Example D

Alternative Method for Synthesis of [4-(3-aminophenyl)-6,7-dimethoxyquinazolin-2-yl]methylamine (Production Example B)

Two hundred grams of crude 3-(2-chloro-6,7-dimethoxyquinazolin-4-yl)phenylamine (content 124 g; 0.394 mol) was suspended in a mixed solution consisting of 1.2 L of tetrahydrofuran and 0.6 L of isopropanol. To the mixture was added 1.2 L of a methylamine solution in methanol, and the mixture was stirred in a SUS autoclave at 90° C. for 15 hours. The reaction mixture was allowed to cool down to 25° C., and concentrated under reduced pressure. To the residue were added 1.0 L of water and 4.0 L of chloroform, and the mixture was stirred at 50° C. for 0.5 hours and allowed to cool down to 25° C. The mixture was filtered through celite to remove the insoluble matter, and the filtrate was transferred to separatory funnel and the organic layer was separated. To the separated organic layer were added 50.0 g of anhydrous magnesium sulfate and 20.0 g of activated carbon, and the mixture was stirred at 50° C. for 1 hour and allowed to cool down to 25° C. The mixture was filtered through celite to remove the insoluble matter, and the filtrate was concentrated under reduced pressure. To the residue was added 904 mL of chloroform, and the mixture was stirred at 50° C. for 1 hour and stirred overnight after turning off the heater. Then the mixture was stirred in an ice bath for 2 hours and precipitated crystals were collected by filtration. The collected crystals were dried at 50° C. under reduced pressure to give 76.3 g of a target product. Yield: 38.7%

Production Example 1

Synthesis of methyl N-[3-(6,7-dimethoxy-2-methylaminoquinazolin-4-yl)phenyl]terephthalamic acid

[Formula 8]

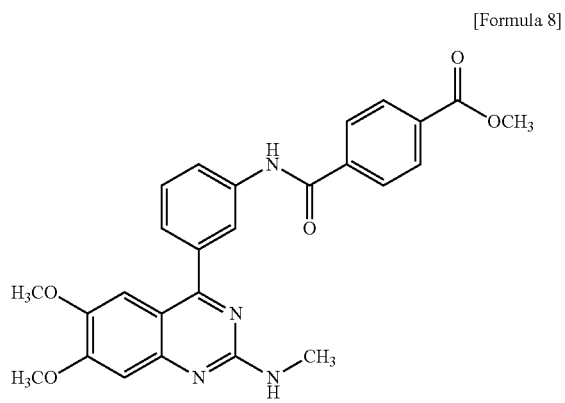 [SMILES: CNc1nc(-c2cccc(NC(=O)c3ccc(C(=O)OC)cc3)c2)c2cc(OC)c(OC)cc2n1]

To a solution of 16.8 g of [4-(3-aminophenyl)-6,7-dimethoxyquinazolin-2-yl]methylamine and 8.6 g of pyridine dissolved in 300 mL of tetrahydrofuran was added 11.8 g of 4-chlorocarbonylbenzoic acid methyl ester at room temperature, followed by stirring for 24 hours. To the reaction mixture was added 100 mL of dimethyl sulfoxide, the mixture was partitioned between a mixed solvent consisting of 2,000 mL of ethyl acetate and 1,000 mL of tetrahydrofuran, and 1,000 mL of a saturated sodium hydrogencarbonate solution, and the organic layer was separated. The water layer was further extracted with a mixed solvent consisting of 500 mL of ethyl acetate and 500 mL of tetrahydrofuran. The combined organic layer was then washed with 1,000 mL of a saturated sodium hydrogencarbonate solution and 1,000 mL of brine in this order, and dried over anhydrous magnesium sulfate. The desiccant was removed by filtration with 100 g of a basic silica gel pad, followed by well washing with 2,000 mL of ethyl acetate. The combined eluent was concentrated under reduced pressure, and the obtained crude product was suspended and triturated in a mixed solvent consisting of 100 mL of tetrahydrofuran and 500 mL of diethyl ether. The precipitated crystals were collected by filtration, washed twice with 100 mL of diethyl ether, and dried under aeration at 50° C. for 5 hours to give 13.8 g of the crystals of the titled compound (yield: 53.2%).

$^1$H-NMR (DMSO-$d_6$) δ (ppm): 2.88 (3H, d, J=4.4 Hz), 3.74 (3H, s), 3.89 (3H, s), 3.92 (3H, s), 6.99 (1H, s), 7.00 (1H, brs), 7.17 (1H, s), 7.46 (1H, d, J=8.0 Hz), 7.55 (1H, t, J=8.0 Hz), 7.87 (1H, brd, J=8.0 Hz), 8.08 (4H, s), 8.20 (1H, brs), 10.61 (1H, s).

Production Example 2

Synthesis of N-[3-(6,7-dimethoxy-2-methylaminoquinazolin-4-yl)phenyl]terephthalamic acid hydrochloride

[Formula 9]

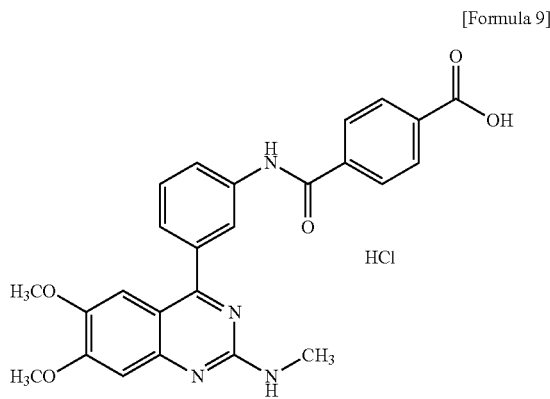 [SMILES: CNc1nc(-c2cccc(NC(=O)c3ccc(C(=O)O)cc3)c2)c2cc(OC)c(OC)cc2n1 ; Cl]

To a solution of 2.5 g of methyl N-[3-(6,7-dimethoxy-2-methylaminoquinazolin-4-yl)phenyl]terephthalamic acid dissolved in a mixed solvent consisting of 50 mL of tetrahydrofuran and 25 mL of methanol was added 11.3 mL of a 5 N sodium hydroxide solution, followed by stirring at room temperature for 12 hours. The reaction mixture was adjusted to be acidic by addition of 5 N hydrochloric acid, and the obtained solid was then filtrated, washed with 10 mL of water and 20 mL of ether, and dried under aeration to give 2.5 g of a target product. Yield: 95.3%.

$^1$H-NMR (DMSO-$d_6$) δ (ppm): 3.05 (3H, brs), 3.82 (3H, s), 3.98 (3H, s), 7.32 (1H, s), 7.54 (1H, brd, J=8.0 Hz), 7.55 (1H, brs), 7.61 (1H, t, J=8.0 Hz), 7.91 (1H, d, J=8.0 Hz), 8.06 (4H, s), 8.35 (1H, brs), 10.71 (1H, s).

Production Example 3

Synthesis of N-[3-(6,7-dimethoxy-2-methylaminoquinazolin-4-yl)phenyl]-N',N'-dimethylterephthalamide

[Formula 10]

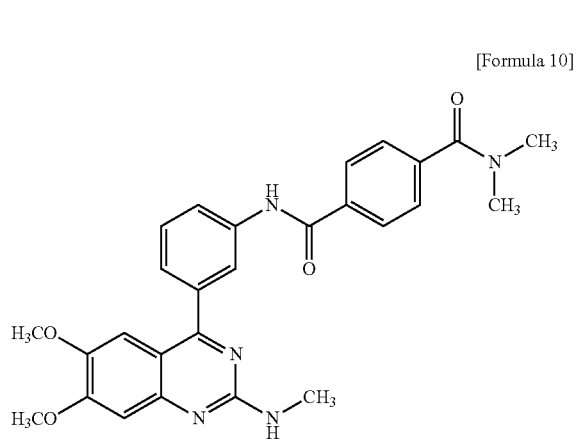 [SMILES: CNc1nc(-c2cccc(NC(=O)c3ccc(C(=O)N(C)C)cc3)c2)c2cc(OC)c(OC)cc2n1]

To a solution of 100 mg of N-[3-(6,7-dimethoxy-2-methylaminoquinazolin-4-yl)phenyl]terephthalamic acid hydrochloride dissolved in 2 mL of dimethylformamide were added 60 mg of WSC, 41 mg of 1-hydroxybenzotriazole, 42 µL of triethylamine, and 10 mg of 4-dimethylaminopyridine, followed by stirring at room temperature for 30 minutes. To the reaction mixture was added 200 µL of a dimethylamine solution in tetrahydrofuran, followed by stirring at room temperature for 15 hours. To the reaction mixture was added 2 mL of tetrahydrofuran, and the reaction mixture was partitioned after addition of a saturated sodium hydrogencarbonate solution. The organic layer was extracted with 10 mL of ethyl acetate, washed with brine, and dried over anhydrous magnesium sulfate. The anhydrous magnesium sulfate was removed by filtration, and the organic layer was concentrated to dryness, and the residue was triturated with a mixed solution consisting of ethyl acetate:n-heptane=1:1. The obtained solid was filtrated, washed with diethyl ether, and dried under aeration to give 85 mg of a target product. Yield: 87%.

$^1$H-NMR (CD$_3$OD) δ (ppm): 3.01 (3H, s), 3.05 (3H, s), 3.13 (3H, s), 3.83 (3H, s), 3.99 (3H, s), 7.11 (1H, s), 7.27 (1H, s), 7.52 (1H, ddd, J=1.6, 1.6, 8.0 Hz), 7.57 (2H, d, J=8.4 Hz), 7.58 (1H, t, J=8.4 Hz), 7.81 (1H, ddd, J=1.6, 2.0, 8.0 Hz), 8.04 (2H, d, J=8.4 Hz), 8.19 (1H, t, J=2.0 Hz).

The following compounds of production examples 4 to 10 were synthesized by methods similar to production example 3, using the compound of production example 2 as a starting substance, and also using the corresponding alcohol or amine.

Production Example 4

Synthesis of ethyl N-[3-(6,7-dimethoxy-2-methylaminoquinazolin-4-yl)phenyl]terephthalamic acid

[Formula 11]

$^1$H-NMR (DMSO-$d_6$) δ (ppm): 1.33 (3H, t, J=7.2 Hz), 2.84 (3H, d, J=4.8 Hz), 3.74 (3H, s), 3.91 (3H, s), 4.34 (2H, q, J=7.2 Hz), 6.99 (1H, s), 7.00 (1H, brs), 7.17 (1H, s), 7.47 (1H, d, J=8.0 Hz), 7.55 (1H, t, J=8.0 Hz), 7.88 (1H, brd, J=8.0 Hz), 8.08 (4H, s), 8.20 (1H, brs), 10.61 (1H, s).

Production Example 5

Synthesis of N-[3-(6,7-dimethoxy-2-methylamino-quinazolin-4-yl)phenyl]-N'-methylterephthalamide

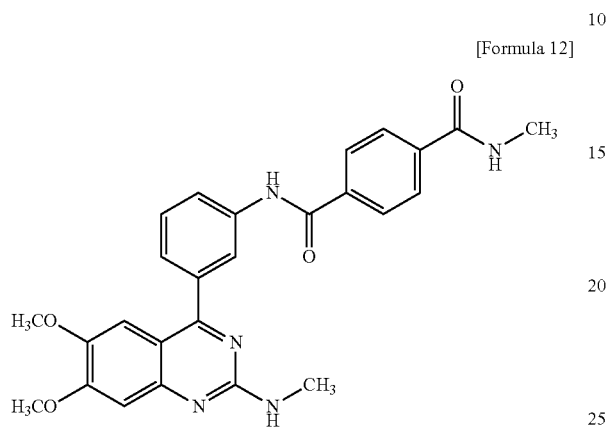

[Formula 12]

$^1$H-NMR (DMSO-d$_6$) δ (ppm): 2.81 (3H, d, J=4.4 Hz), 2.90 (3H, d, J=5.2 Hz), 3.75 (3H, s), 3.93 (3H, s), 6.99 (1H, s), 7.01 (1H, brs), 7.18 (1H, s), 7.46 (1H, d, J=8.0 Hz), 7.55 (1H, t, J=8.0 Hz), 7.89 (1H, brd, J=8.0 Hz), 7.96 (2H, d, J=8.8 Hz), 8.04 (2H, d, J=8.8 Hz), 8.21 (1H, t, J=1.6 Hz), 8.59 (1H, br), 10.53 (1H, s).

Production Example 6

Synthesis of propyl N-[3-(6,7-dimethoxy-2-methylaminoquinazolin-4-yl)phenyl]terephthalamic acid

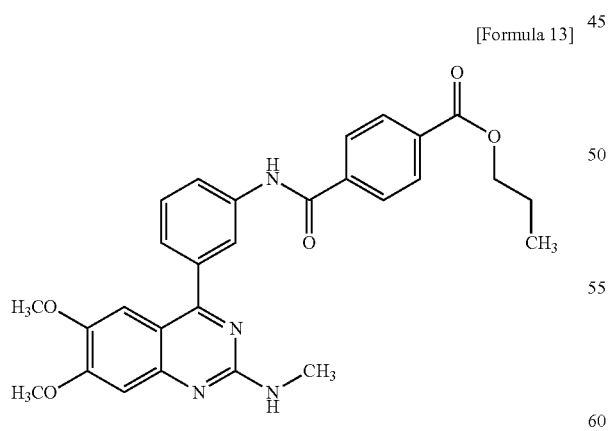

[Formula 13]

$^1$H-NMR (DMSO-d$_6$) δ (ppm): 0.99 (3H, t, J=7.6 Hz), 1.76 (2H, m), 2.90 (3H, d, J=5.2 Hz), 3.76 (3H, s), 3.93 (3H, s), 4.28 (2H, t, J=6.8 Hz), 7.01 (1H, s), 7.03 (1H, brs), 7.19 (1H, s), 7.49 (1H, d, J=8.0 Hz), 7.57 (1H, t, J=8.0 Hz), 7.90 (1H, brd, J=8.0 Hz), 8.11 (4H, s), 8.22 (1H, brs), 10.65 (1H, s).

Production Example 7

Synthesis of isopropyl N-[3-(6,7-dimethoxy-2-methylaminoquinazolin-4-yl)phenyl]terephthalamic acid

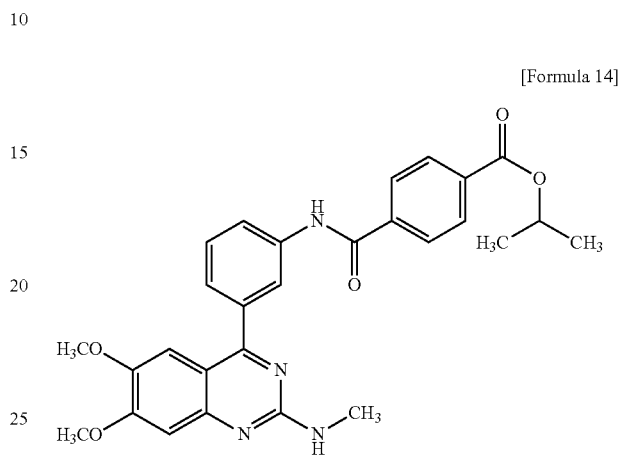

[Formula 14]

$^1$H-NMR (DMSO-d$_6$) δ (ppm): 1.35 (6H, d, J=6.4 Hz), 2.90 (3H, d, J=5.2 Hz), 3.76 (3H, s), 3.93 (3H, s), 5.18 (1H, m), 7.01 (1H, s), 7.03 (1H, brs), 7.19 (1H, s), 7.49 (1H, d, J=8.0 Hz), 7.57 (1H, t, J=8.0 Hz), 7.91 (1H, brd, J=8.0 Hz), 8.09 (4H, s), 8.22 (1H, brs), 10.65 (1H, s).

Production Example 8

Synthesis of N-[3-(6,7-dimethoxy-2-methylaminoquinazolin-4-yl]-N'-ethylterephthalamide

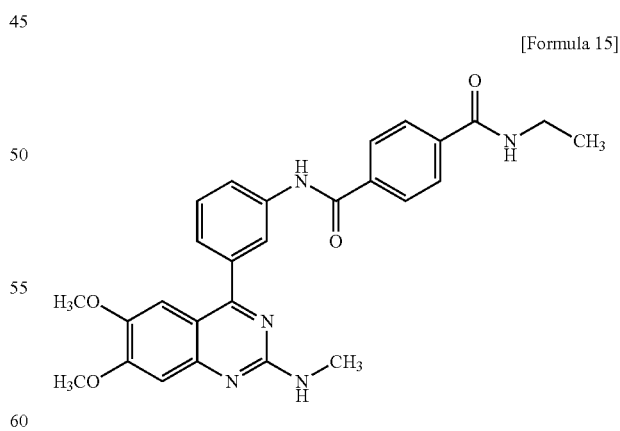

[Formula 15]

$^1$H-NMR (DMSO-d$_6$) δ (ppm): 1.15 (3H, t, J=7.2 Hz), 2.91 (3H, d, J=4.8 Hz), 3.32 (2H, m), 3.76 (3H, s), 3.94 (3H, s), 7.01 (1H, s), 7.03 (1H, brs), 7.19 (1H, s), 7.48 (1H, d, J=8.0 Hz), 7.57 (1H, t, J=8.0 Hz), 7.91 (1H, brd, J=8.0 Hz), 7.98 (2H, d, J=8.4 Hz), 8.06 (2H, d, J=8.4 Hz), 8.22 (1H, brs), 8.64 (1H, t, J=5.6 Hz), 10.55 (1H, s).

Production Example 9

Synthesis of N-[3-(6,7-dimethoxy-2-methylamino-quinazolin-4-yl)phenyl]-N'-propylterephthalamide

[Formula 16]

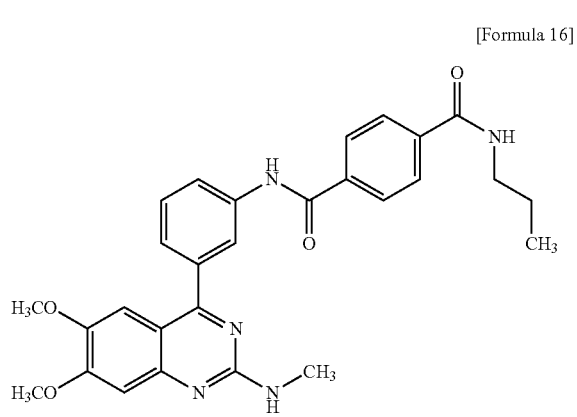 [SMILES: CCCNC(=O)c1ccc(C(=O)Nc2cccc(-c3nc(NC)nc4cc(OC)c(OC)cc34)c2)cc1]

$^1$H-NMR (DMSO-d$_6$) δ (ppm): 0.91 (3H, t, J=7.6 Hz), 1.56 (2H, m), 2.91 (3H, d, J=4.8 Hz), 3.25 (2H, q, J=6.0 Hz), 3.76 (3H, s), 3.94 (3H, s), 7.01 (1H, s), 7.02 (1H, brs), 7.19 (1H, s), 7.48 (1H, d, J=8.0 Hz), 7.57 (1H, t, J=8.0 Hz), 7.91 (1H, brd, J=8.0 Hz), 7.98 (2H, d, J=8.4 Hz), 8.06 (2H, d, J=8.4 Hz), 8.22 (1H, brs), 8.62 (1H, t, J=6.0 Hz), 10.55 (1H, s).

Production Example 10

Synthesis of N-[3-(6,7-dimethoxy-2-methylamino-quinazolin-4-yl)phenyl]-N'-isopropylterephthalamide

[Formula 17]

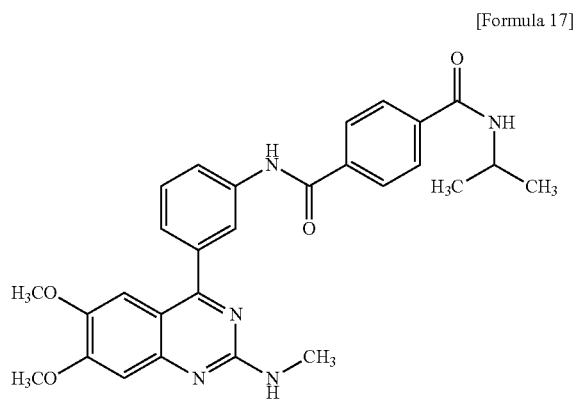 [SMILES: CNc1nc(-c2cccc(NC(=O)c3ccc(C(=O)NC(C)C)cc3)c2)c2cc(OC)c(OC)cc2n1]

$^1$H-NMR (DMSO-d$_6$) δ (ppm): 1.19 (6H, d, J=6.8 Hz), 2.91 (3H, d, J=4.8 Hz), 3.76 (3H, s), 3.94 (3H, s), 4.12 (1H, m), 7.01 (1H, s), 7.02 (1H, brs), 7.19 (1H, s), 7.48 (1H, d, J=8.0 Hz), 7.57 (1H, t, J=8.0 Hz), 7.92 (1H, brd, J=8.0 Hz), 7.98 (2H, d, J=8.4 Hz), 8.05 (2H, d, J=8.4 Hz), 8.22 (1H, brs), 8.34 (1H, d, J=7.6 Hz), 10.55 (1H, s).

Production Example 11

Synthesis of methyl N-[3-(6,7-dimethoxy-2-methylaminoquinazolin-4-yl)phenyl]isophthalic acid

[Formula 18]

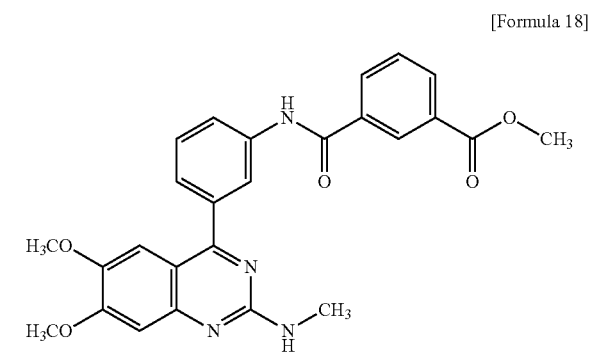 [SMILES: CNc1nc(-c2cccc(NC(=O)c3cccc(C(=O)OC)c3)c2)c2cc(OC)c(OC)cc2n1]

A mixture of 2.00 g (6.44 mmol) of 3-(2-chloro-6,7-dimethoxyquinazolin-4-yl)phenylamine, 1.75 g (9.71 mmol) of isophthalic acid monomethyl ester, 2.7 mL of triethylamine, 1.00 g of 1-hydroxybenzotriazole hydrate, and 2.00 g of WSC hydrochloride, was suspended in 15 mL of dimethylformamide, followed by stirring at room temperature overnight. The reaction mixture was poured into water, and extracted with ethyl acetate. The organic layer was washed with brine, and dried over magnesium sulfate. After filtration, the residue obtained by solvent distillation under reduced pressure was then subjected to silica gel column chromatography (ethyl acetate-heptane). Thereafter, a solid precipitated with ethyl acetate-hexane was collected by filtration, and dried under aeration to give 2.65 g of the titled compound (yield: 87%).

$^1$H-NMR (DMSO-d$_6$) δ (ppm): 2.91 (3H, d, J=4.8 Hz), 3.76 (3H, s), 3.92 (3H, s), 3.93 (3H, s), 7.01 (1H, s), 7.02 (1H, brs), 7.19 (1H, s), 7.48 (1H, brd, J=8.0 Hz), 7.57 (1H, t, J=8.0 Hz), 7.72 (1H, t, J=8.0 Hz), 7.92 (1H, brd, J=8.0 Hz), 8.17 (1H, brd, J=8.0 Hz), 8.22 (1H, t, J=1.6 Hz), 8.26 (1H, brd, J=8.0 Hz), 8.56 (1H, t, J=1.6 Hz), 10.67 (1H, s).

Production Example 12

Synthesis of N-[3-(6,7-dimethoxy-2-methylamino-quinazolin-4-yl)phenyl]isophthalic acid

[Formula 19]

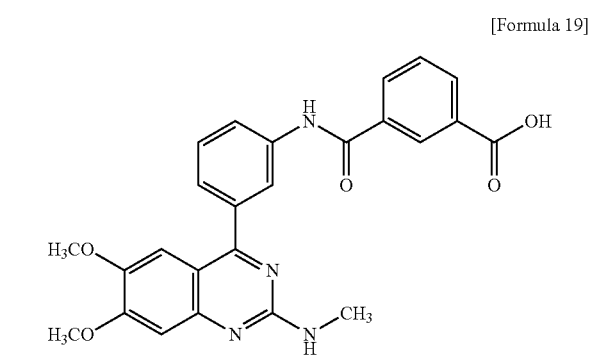 [SMILES: CNc1nc(-c2cccc(NC(=O)c3cccc(C(=O)O)c3)c2)c2cc(OC)c(OC)cc2n1]

To a solution of 2.49 g (5.27 mmol) of the compound of production example 11 as obtained above dissolved in a mixed solvent consisting of 40 mL of tetrahydrofuran and 40 mL of ethanol was added 15 mL of a 1 N sodium hydroxide aqueous solution, followed by stirring at room temperature overnight. The reaction mixture was neutralized with 15 mL of 1 N hydrochloric acid, and 60 mL of water was added thereto. The precipitated solid was collected by filtration, and dried under hot air to give 3.31 g of the titled compound.

$^1$H-NMR (DMSO-$d_6$) δ (ppm): 2.91 (3H, d, J=4.8 Hz), 3.76 (3H, s), 3.94 (3H, s), 7.01 (1H, s), 7.02 (1H, brs), 7.20 (1H, s), 7.48 (1H, brd, J=8.0 Hz), 7.57 (1H, t, J=8.0 Hz), 7.69 (1H, t, J=8.0 Hz), 7.92 (1H, brd, J=8.0 Hz), 8.15 (1H, brd, J=8.0 Hz), 8.22 (1H, brd, J=8.0 Hz), 8.23 (1H, t, J=1.6 Hz), 8.56 (1H, t, J=1.6 Hz), 10.65 (1H, s).

The following compounds of production examples 13 to 19 were synthesized by methods similar to production example 3, using the compound of the aforementioned production example 12 as a starting substance, and also using the corresponding alcohol or amine.

Production Example 13

Synthesis of ethyl N-[3-(6,7-dimethoxy-2-methylaminoquinazolin-4-yl)phenyl]isophthalic acid

[Formula 20]

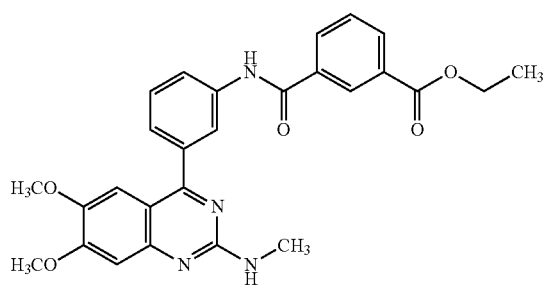

$^1$H-NMR (DMSO-$d_6$) δ (ppm): 1.36 (3H, t, J=7.2 Hz), 2.91 (3H, d, J=4.8 Hz), 3.76 (3H, s), 3.93 (3H, s), 4.38 (2H, q, J=7.2 Hz), 7.01 (1H, s), 7.02 (1H, brs), 7.19 (1H, s), 7.48 (1H, brd, J=8.0 Hz), 7.57 (1H, t, J=8.0 Hz), 7.71 (1H, t, J=8.0 Hz), 7.92 (1H, brd, J=8.0 Hz), 8.17 (1H, brd, J=8.0 Hz), 8.22 (1H, t, J=1.6 Hz), 8.25 (1H, brd, J=8.0 Hz), 8.54 (1H, t, J=1.6 Hz), 10.67 (1H, s).

Production Example 14

Synthesis of propyl N-[3-(6,7-dimethoxy-2-methylaminoquinazolin-4-yl)phenyl]isophthalic acid

[Formula 21]

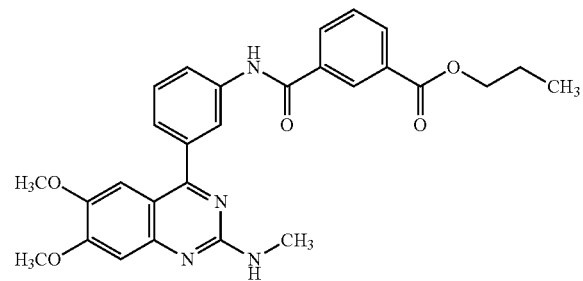

$^1$H-NMR (DMSO-$d_6$) δ (ppm): 0.99 (3H, t, J=7.2 Hz), 1.76 (2H, qt, J=7.2, 6.8 Hz), 2.91 (3H, d, J=4.4 Hz), 3.76 (3H, s), 3.93 (3H, s), 4.29 (2H, t, J=6.8 Hz), 7.01 (1H, s), 7.02 (1H, brs), 7.19 (1H, s), 7.49 (1H, brd, J=8.0 Hz), 7.57 (1H, t, J=8.0 Hz), 7.72 (1H, t, J=8.0 Hz), 7.91 (1H, brd, J=8.0 Hz), 8.18 (1H, brd, J=8.0 Hz), 8.22 (1H, t, J=1.6 Hz), 8.25 (1H, brd, J=8.0 Hz), 8.54 (1H, t, J=1.6 Hz), 10.67 (1H, s).

Production Example 15

Synthesis of isopropyl N-[3-(6,7-dimethoxy-2-methylaminoquinazolin-4-yl)phenyl]isophthalic acid

[Formula 22]

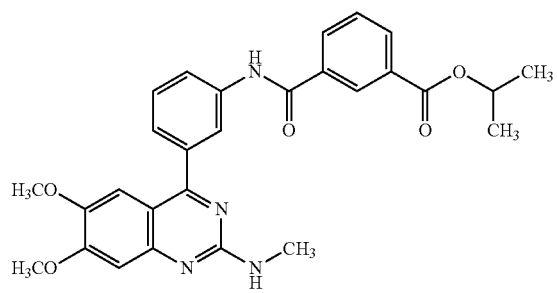

$^1$H-NMR (DMSO-$d_6$) δ (ppm): 1.36 (6H, d, J=6.4 Hz), 2.91 (3H, d, J=4.8 Hz), 3.76 (3H, s), 3.93 (3H, s), 5.19 (1H, septet, J=6.4 Hz), 7.01 (1H, s), 7.02 (1H, brs), 7.19 (1H, s), 7.48 (1H, brd, J=8.0 Hz), 7.57 (1H, t, J=8.0 Hz), 7.71 (1H, t, J=8.0 Hz), 7.91 (1H, brd, J=8.0 Hz), 8.15 (1H, brd, J=8.0 Hz), 8.21 (1H, t, J=1.6 Hz), 8.24 (1H, brd, J=8.0 Hz), 8.52 (1H, t, J=1.6 Hz), 10.67 (1H, s).

Production Example 16

Synthesis of N-[3-(6,7-dimethoxy-2-methylaminoquinazolin-4-yl)phenyl]-N'-methylisophthalamide

[Formula 23]

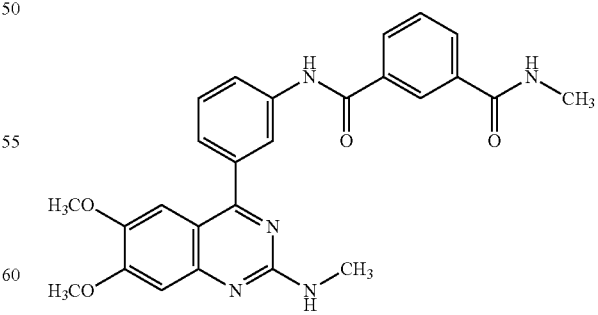

$^1$H-NMR (DMSO-$d_6$) δ (ppm): 2.82 (3H, d, J=4.4 Hz), 2.91 (3H, d, J=4.8 Hz), 3.76 (3H, s), 3.93 (3H, s), 7.01 (1H, s), 7.02 (1H, brs), 7.19 (1H, s), 7.48 (1H, brd, J=8.0 Hz), 7.57 (1H, t, J=8.0 Hz), 7.64 (1H, t, J=8.0 Hz), 7.91 (1H, brd, J=8.0

Hz), 8.02 (1H, brd, J=8.0 Hz), 8.10 (1H, brd, J=8.0 Hz), 8.22 (1H, t, J=1.6 Hz), 8.42 (1H, t, J=1.6 Hz), 8.60 (1H, brq, J=4.8 Hz), 10.58 (1H, s).

Production Example 17

Synthesis of N-[3-(6,7-dimethoxy-2-methylamino-quinazolin-4-yl)phenyl]-N'-ethylisophthalamide

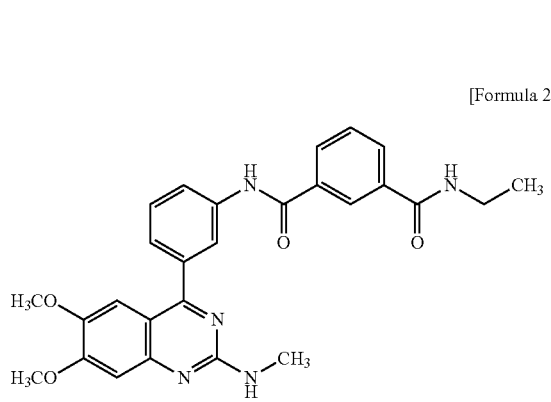

[Formula 24]

$^1$H-NMR (DMSO-d$_6$) δ (ppm): 1.15 (3H, t, J=7.2 Hz), 2.91 (3H, d, J=4.4 Hz), 3.33 (2H, q, J=7.2 Hz), 3.76 (3H, s), 3.93 (3H, s), 7.01 (1H, s), 7.02 (1H, brs), 7.19 (1H, s), 7.48 (1H, brd, J=8.0 Hz), 7.57 (1H, t, J=8.0 Hz), 7.63 (1H, t, J=8.0 Hz), 7.92 (1H, brd, J=8.0 Hz), 8.03 (1H, brd, J=8.0 Hz), 8.09 (1H, brd, J=8.0 Hz), 8.22 (1H, t, J=1.6 Hz), 8.42 (1H, t, J=1.6 Hz), 8.63 (1H, brt, J=5.4 Hz), 10.58 (1H, s).

Production Example 18

Synthesis of N-[3-(6,7-dimethoxy-2-methylamino-quinazolin-4-yl)phenyl]-N'-propylisophthalamide

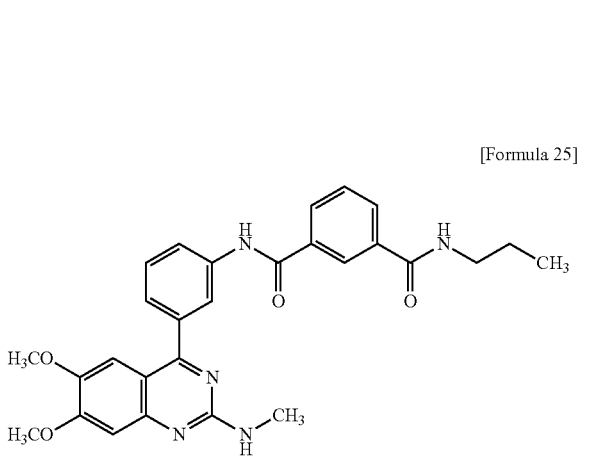 [SMILES: CCCNC(=O)c1cccc(C(=O)Nc2cccc(-c3nc(NC)nc4cc(OC)c(OC)cc34)c2)c1]

[Formula 25]

$^1$H-NMR (DMSO-d$_6$) δ (ppm): 0.91 (3H, t, J=7.2 Hz), 1.56 (2H, qt, J=7.2, 6.4 Hz), 2.91 (3H, d, J=4.4 Hz), 3.25 (2H, dt, J=6.4, 5.4 Hz), 3.76 (3H, s), 3.93 (3H, s), 7.01 (1H, s), 7.02 (1H, brs), 7.19 (1H, s), 7.48 (1H, brd, J=8.0 Hz), 7.57 (1H, t, J=8.0 Hz), 7.63 (1H, t, J=8.0 Hz), 7.92 (1H, brd, J=8.0 Hz), 8.04 (1H, brd, J=8.0 Hz), 8.09 (1H, brd, J=8.0 Hz), 8.22 (1H, t, J=1.6 Hz), 8.42 (1H, t, J=1.6 Hz), 8.62 (1H, brt, J=5.4 Hz), 10.59 (1H, s).

Production Example 19

Synthesis of N-[3-(6,7-dimethoxy-2-methylamino-quinazolin-4-yl)phenyl]-N'-isopropylisophthalamide

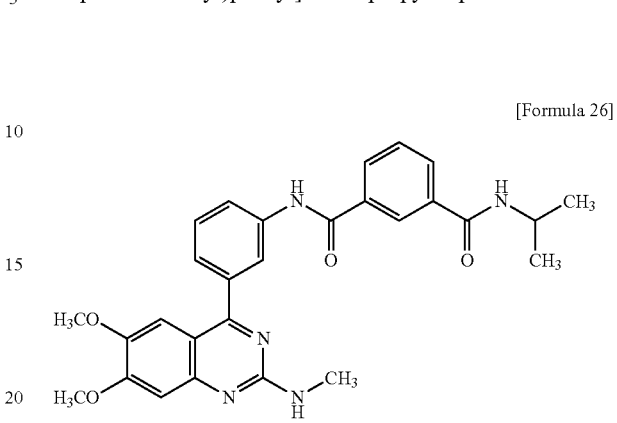

[Formula 26]

$^1$H-NMR (DMSO-d$_6$) δ (ppm): 1.19 (6H, d, J=6.4 Hz), 2.91 (3H, d, J=4.4 Hz), 3.76 (3H, s), 3.93 (3H, s), 4.13 (1H, septet, J=6.4 Hz), 7.01 (1H, s), 7.02 (1H, brs), 7.19 (1H, s), 7.48 (1H, brd, J=8.0 Hz), 7.57 (1H, t, J=8.0 Hz), 7.62 (1H, t, J=8.0 Hz), 7.93 (1H, brd, J=8.0 Hz), 8.04 (1H, brd, J=8.0 Hz), 8.08 (1H, brd, J=8.0 Hz), 8.22 (1H, t, J=1.6 Hz), 8.40 (1H, brd), 8.41 (1H, t, J=1.6 Hz), 10.59 (1H, s).

Production Example 20

N-[3-(6,7-dimethoxy-2-methylaminoquinazolin-4-yl)phenyl]terephthalamic acid 2-methoxyethyl ester

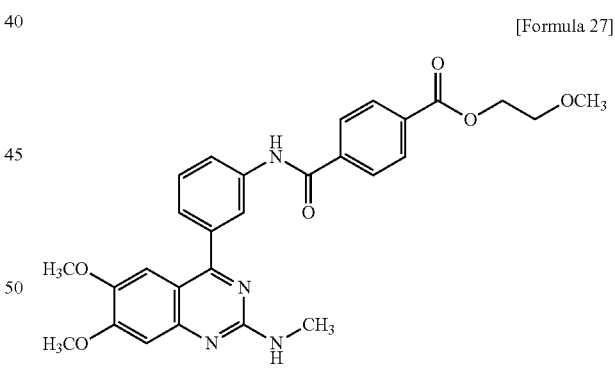

[Formula 27]

A mixture consisting of 55 mg (0.11 mmol) of N-[3-(6,7-dimethoxy-2-methylaminoquinazolin-4-yl)phenyl]terephthalamic acid hydrochloride, 40 µL (0.51 mmol) of 2-methoxyethanol, 47 µL of triethylamine, 17 mg of 1-hydroxybenzotriazole hydrate, and 35 mg of WSC hydrochloride, was suspended in 2 mL of dimethylformamide, followed by stirring at room temperature overnight. The reaction mixture was poured into water, and extracted with ethyl acetate. The organic layer was washed with brine, and was then dried over magnesium sulfate. The residue obtained by filtration and solvent distillation under reduced pressure was subjected to silica gel column chromatography (ethyl acetate-heptane). Thereafter, a solid precipitated with ethyl acetate-hexane was collected by filtration, and was dried under aeration to give 40 mg of the titled compound (yield: 70%).

¹H-NMR (DMSO-d₆) δ (ppm): 2.91 (3H, d, J=4.8 Hz), 3.32 (3H, s), 3.69 (2H, m), 3.76 (3H, s), 3.93 (3H, s), 4.45 (2H, m), 7.01 (1H, s), 7.03 (1H, brs), 7.19 (1H, s), 7.49 (1H, brd, J=7.6 Hz), 7.57 (1H, t, J=7.6 Hz), 7.90 (1H, brd, J=7.6 Hz), 8.11 (4H, s), 8.12 (1H, t, J=1.8 Hz), 10.65 (1H, s).

Production Example 21

N-[3-(6,7-dimethoxy-2-methylaminoquinazolin-4-yl)phenyl]isophthalamic acid 2-methoxyethyl ester

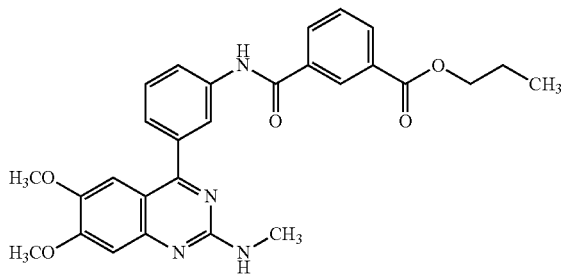

[Formula 28]

The titled compound was obtained by a method that was equivalent to a method similar to production example 3 using the compound of production example 12 as a starting substance and also using 2-methoxyethanol.

¹H-NMR (DMSO-d₆) δ (ppm): 2.91 (3H, d, J=4.8 Hz), 3.32 (3H, s), 3.69 (2H, m), 3.76 (3H, s), 3.93 (3H, s), 4.46 (2H, m), 7.01 (1H, s), 7.03 (1H, brs), 7.19 (1H, s), 7.49 (1H, brd, J=8.0 Hz), 7.57 (1H, t, J=8.0 Hz), 7.73 (1H, t, J=8.0 Hz), 7.92 (1H, brd, J=8.0 Hz), 8.17 (1H, dt, J=8.0, 1.6 Hz), 8.22 (1H, t, J=1.6 Hz), 8.26 (1H, dt, J=8.0, 1.6 Hz), 8.54 (1H, t, J=1.6 Hz), 10.68 (1H, s).

Production Example 22

Synthesis of t-butyl [3-(2-chloro-6,7-dimethoxyquinazolin-4-yl)phenyl]carbamate

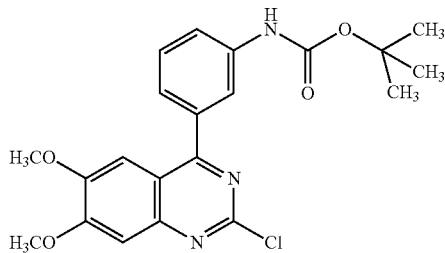

[Formula 29]

To a mixture of 1.00 g (3.86 mmol) of 2,4-dichloro-6,7-dimethoxyquinazoline, 1.14 g (4.63 mmol) of 3-(N-t-butoxycarbonylamino)phenyl borate, tetrahydrofuran (25 mL), and 2 M sodium carbonate aqueous solution (5 mL) were added palladium acetate (8.84 mg) and 1,1'-bis(diphenylphosphino)ferrocene (21.4 mg) in this order, and the mixture was stirred at 60° C. for 6.5 hours under a nitrogen atmosphere. The reaction solution was allowed to cool, and ethyl acetate (25 mL) and 5% w/w sodium chloride solution (20 mL) were added to extract the organic layer. The organic layer was washed twice with 5% w/w sodium chloride solution (20 mL) and then concentrated under reduced pressure. To the concentration residue were added ethyl acetate (1 mL) and 2-propanol (4 mL), and the mixture was suspended by stirring at 40° C. for 0.5 hours. The suspension was cooled, and the precipitated crystals were collected by filtration and dried to give 1.48 g of a target product (yield: 91.5%, HPLC purity: 99.02%).

¹H-NMR (CDCl₃) δ (ppm): 1.52 (9H, s), 3.97 (3H, s), 4.07 (3H, s), 6.62 (1H, br), 7.33 (1H, s), 7.38-7.43 (1H, m), 7.48-7.53 (3H, m), 8.00 (1H, br). ESI MS: m/z 438 (M+Na)⁺.

Production Example 3

Synthesis of t-butyl {3-[6,7-dimethoxy-2-(methylamino)quinazolin-4-yl]phenyl}carbamate

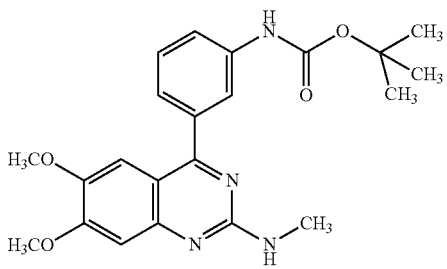

[Formula 30]

In a SUS autoclave were placed 420 mg (1.00 mmol) of t-butyl [3-(2-chloro-6,7-dimethoxyquinazolin-4-yl)phenyl]carbamate, tetrahydrofuran (2.5 mL), and 2-propanol (1.25 mL), to this mixture was added a methanol solution (2.5 mL) of 40% methylamine, and the mixture was stirred at 90° C. for 8 hours. The reaction mixture was allowed to cool and then poured into a mixed solution of ethyl acetate (40 mL), tetrahydrofuran (40 mL), and 5% w/w sodium chloride solution (50 mL) to extract the organic layer. The organic layer was washed with 5% w/w sodium chloride solution (50 mL) and then concentrated under reduced pressure. To the concentration residue was added t-butyl methyl ether (2.1 mL), and the mixture was crystallized with a spatula and then stirred at room temperature for 3 hours. The precipitated crystals were collected by filtration and dried to give 348 mg of a target product (yield: 83.8%, HPLC purity: 98.70%).

¹H-NMR (CDCl₃) δ (ppm): 1.52 (9H, s), 3.12 (3H, d, J=5.2 Hz), 3.85 (3H, s), 4.03 (3H, s), 5.11 (1H, brd, J=5.2 Hz), 6.59 (1H, br), 7.07 (1H, s), 7.19 (1H, s), 7.36-7.48 (3H, m), 7.80 (1H, br). ESI MS: m/z 433 (M+Na)⁺.

Production Example 24

Synthesis of [4-(3-aminophenyl)-6,7-dimethoxyquinazolin-2-yl]methylamine

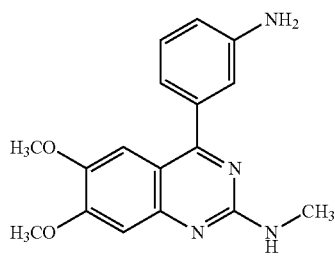

[Formula 31]

Under a nitrogen atmosphere, 100 mg (0.24 mmol) of t-butyl {3-[6,7-dimethoxy-2-(methylamino)quinazolin-4-yl]phenyl}carbamate was suspended in dichloromethane (1 mL), to the suspension was dropwise added trifluoroacetic acid (0.2 mL) while cooling to 0° C., the mixture was stirred at the same temperature for 1 hour followed by stirring at room temperature for 6 hours. While cooling with ice water, 0.5 N aqueous sodium hydroxide solution (5.94 mL) was added dropwise, and into the reaction mixture were poured ethyl acetate (10 mL), tetrahydrofuran (10 mL), and 5% w/w sodium chloride solution (20 mL) to extract the organic layer. The organic layer was washed twice with 5% w/w sodium chloride solution (20 mL) and then concentrated under reduced pressure. To the concentration residue was added t-butyl methyl ether (0.6 mL), and the mixture was crystallized with a spatula and stirred at room temperature for 4 hours. The precipitated crystals were collected by filtration and dried to give 66.1 mg of a target product (yield: 87.2%, HPLC purity: 98.27%).

$^1$H-NMR (CDCl$_3$) δ (ppm): 3.12 (3H, d, J=5.2 Hz), 3.80 (2H, brs), 3.82 (3H, s), 4.03 (3H, s), 5.30 (1H, br), 6.83 (1H, dd, J=1.6, 8.0 Hz), 6.99 (1H, t, J=1.6 Hz), 7.04 (1H, brd, J=8.0 Hz), 7.07 (1H, s), 7.15 (1H, s), 7.30 (1H, t, J=8.0 Hz).

Production Example 25

A Method for Producing Anhydrous Crystals 1 of methyl N-[3-(6,7-dimethoxy-2-methylaminoquinazolin-4-yl)phenyl]terephthalamic acid A suspension consisting of 10.00 g (55.51 mmol) of monomethyl terephthalate and 90 mL of 1,2-dimethoxyethane was stirred, while it is cooled in a cold bath at 10° C. To the suspension were added 2.0 mL of N,N-dimethylformamide and 6.61 g (52.75 mmol) of thionyl chloride in this order. The suspension was stirred under heating at 60° C. to 65° C. for 1 hour, and allowed to cool. Thereafter, the suspension was further stirred while it was cooled in an ice bath. Subsequently, 6.83 g (52.82 mmol) of diisopropylethylamine was added dropwise to the mixture. Subsequently, the reaction mixture was stirred at room temperature. Thirty minutes after the internal temperature had reached 20° C., stirring was terminated. The reaction mixture was placed in a 200-mL eggplant flask, followed by measurement to yield 109.49 g of a mixed solution consisting of [monomethyl terephthalate chloride/diisopropylethylamine] (the content of monomethyl terephthalate chloride: 8.89 g) as a slight tannish solution.

Subsequently, a suspension consisting of 9.50 g (30.00 mmol) of [4-(3-aminophenyl)-6,7-dimethoxyquinazolin-2-yl]methylamine and 380 mL of tetrahydrofuran was stirred, while it was cooled at 0° C. To the suspension was added dropwise over 1 hour, 80.71 g of the above mixed solution consisting of [monomethyl terephthalate chloride/diisopropylethylamine] (the content of monomethyl terephthalate chloride: 6.55 g; 33.00 mmol). The mixture was then stirred at 0° C. for 11 hours. Thereafter, 190 mL of ethyl acetate was added to the reaction mixture while cooling at 0° C., and 380 g of a 5% sodium hydrogencarbonate solution was then added dropwise thereto. The reaction mixture was transferred into a separatory funnel, and 190 mL of ethyl acetate was added. After extraction, the organic layer was separated, and washed with 190 g of a 5% sodium chloride solution and 190 mL of water (twice) in this order. The organic layer was concentrated under reduced pressure at 40° C. To the residue was added 143 mL of methanol, and the mixture was stirred while heating to 40° C. Thirty-three minutes after initiation of stirring, the temperature of an oil bath was set at 75° C. Thereafter, 30 minutes after the internal temperature had exceeded 60° C., the temperature of the oil bath was set at 50° C. When the internal temperature was decreased to 55° C., 143 mL of 2-propanol was added dropwise thereto. Subsequently, the internal temperature was gradually cooled to 27.3° C., and the mixture was then stirred at 20° C. for 17 hours. The precipitated crystals were subjected to vacuum filtration, and the resultant was washed with a mixed solution consisting of 14.3 mL of methanol and 14.3 mL of 2-propanol. The resultant was aspirated with a vacuum line for 10 minutes for deliquoring to give 15.72 g of a crude target product (wet body; the content of a product of interest: 13.31 g) as pale yellow crystals (yield: 93.9%).

A suspension consisting of 15.48 g of the crude product of interest (wet body) (the content of the product of interest: 13.11 g; 27.00 mmol) and 40 mL of dimethyl sulfoxide was stirred under heating at 60° C., and the crystals were dissolved. The obtained solution was subjected to clarifying filtration, and washed with 10 mL of dimethyl sulfoxide. The filtrate was transferred into a 1,000-mL four-necked glass vessel, which had previously been heated with a 60° C. hot water jacket, and the residue was washed with 10 mL of dimethyl sulfoxide. The mixture was then stirred under heating at 60° C. Thereafter, 119 mL of 2-propanol was added dropwise to this solution, and 49.3 mg of seed crystals of the product of interest was placed in the mixture. Thereafter, 60 mL of 2-propanol was further added dropwise to the mixture. This suspension was stirred at 60° C. for 2 hours, the temperature of the jacket was set at 80° C., and the suspension was continuously stirred under heating for 16.5 hours. Subsequently, 120 mL of 2-propanol was added dropwise to the suspension, and 3 hours later, 362 mL of 2-propanol was further added dropwise thereto. Thereafter, the mixture was gradually cooled to 20° C. (10° C./h), and it was then stirred at the same temperature. Fifty nine point five hours later, the precipitated crystals were collected by filtration, and the crystals were washed with a mixed solution consisting of 2.6 mL of dimethyl sulfoxide and 24 mL of 2-propanol. The crystals were further washed with 40 mL of 2-propanol, and were then aspirated with a vacuum line for deliquoring. The obtained crystals were dried under reduced pressure to give 9.84 g of a target product as yellow crystals (yield: 73.7%).

The measurement of powder X-ray diffraction pattern of the obtained crystals was carried out according to the powder X-ray diffraction measurement method described in General Tests in the Japanese Pharmacopoeia, under the following conditions.
(Apparatus)
Rigaku X-ray DTA System: RINT-2000 (manufactured by Rigaku Corporation)
(Operation Method)
A sample was ground in an agate mortar, and then sampled on a copper board. Thereafter, measurement was carried out under the following conditions.
X-ray used: CuKα ray
Tube voltage: 40 kV
Tube current: 200 mA
Divergent slit: ½ deg
Receiving slit: 0.3 mm
Scattering slit: ½ deg
Scanning rate: 2°/min
Scanning step: 0.02°
Scanning range (2θ): 5° to 40°

Figure 3:
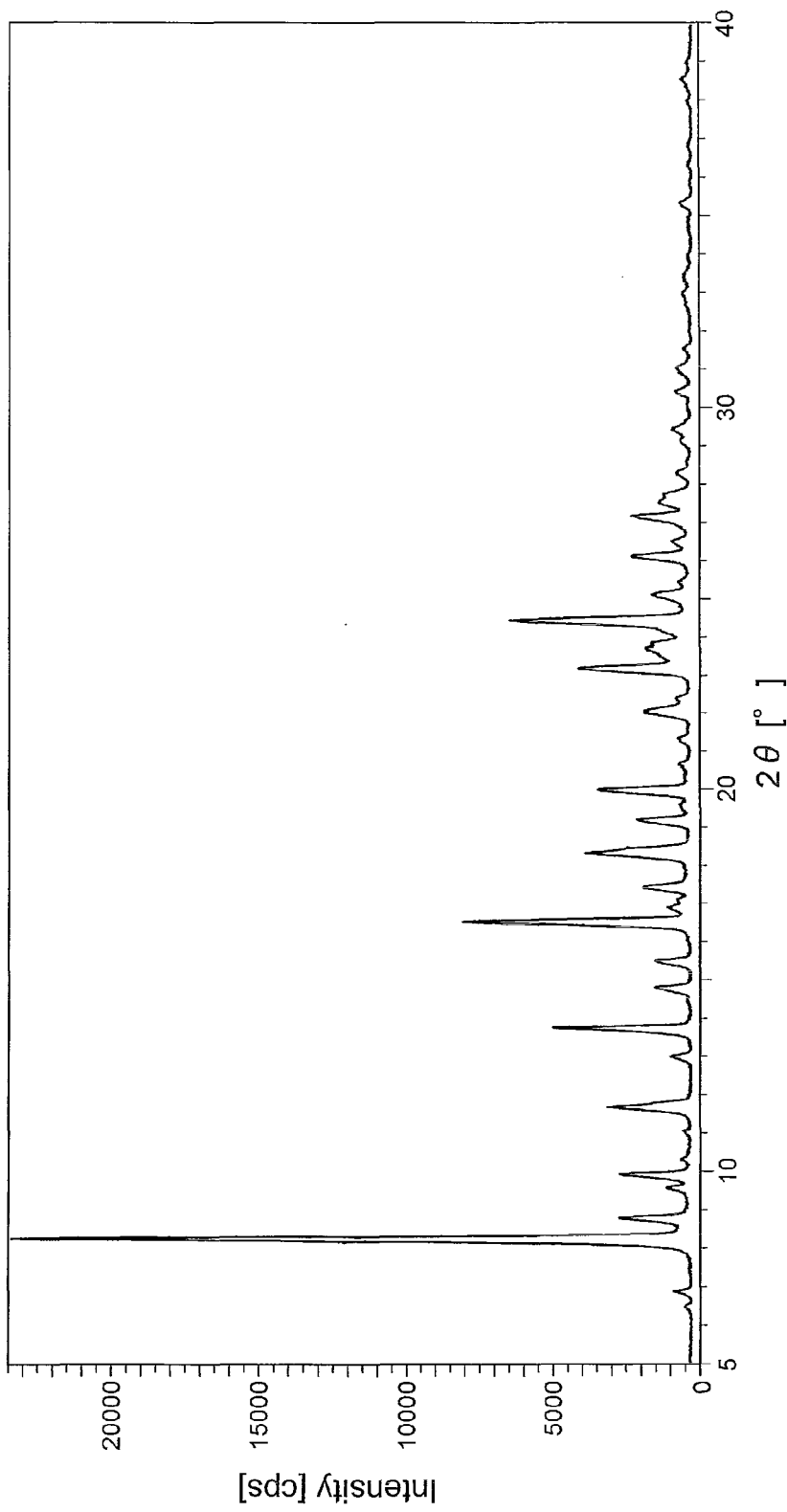
FIG. 3 is the powder X-ray diffraction patterns of the crystals obtained in Production example 25.

The powder X-ray diffraction patterns of the obtained crystals is shown in FIG. 3. The major peaks of diffraction angles (2θ) are 8.2°, 16.5° and 24.5°.

Production Example 26

Synthesis of methyl N-[3-(6,7-dimethoxy-2-methylaminoquinazolin-4-yl)phenyl]terephthalamic acid

[Formula 32]

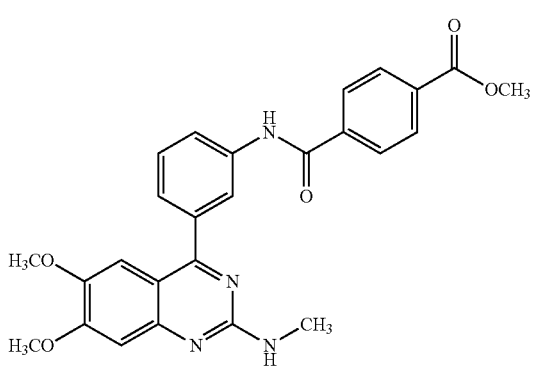

(1) Preparation of "terephthalic acid monomethyl ester chloride/N,N-diisopropylethylamine" Solution A suspension of 1.997 kg (11.08 mol) of terephthalic acid monomethyl ester in 15.60 kg of 1,2-dimethoxyethane was stirred in a nitrogen atmosphere while being cooled at 10° C. To the suspension was added 400 mL (5.17 mol) of N,N-dimethylformamide and 1.323 kg (10.56 mol) of thionyl chloride in this order, and then the container was washed with 1.00 L of 1,2-dimethoxyethane. The suspension was stirred under heating at 60 to 73° C. for 1 hour and 2 minutes and then stirred while being cooled. 1.36 kg (10.52 mol) of N,N-diisopropylethylamine was added dropwise to the solution while cooling at 0° C., and the container was washed with 1.00 L of 1,2-dimethoxyethane. Then the reaction solution was stirred at 25° C., and the stirring was stopped 38 minutes after the internal temperature had reached 20° C. The reaction mixture was transferred into a plastic container, and 22.00 kg of "monomethyl terephthalate chloride/N,N-diisopropylethylamine" solution (terephthalic acid monomethyl ester chloride content: 1.84 kg) was obtained as a slightly tannish solution.

(2) Synthesis of methyl N-[3-(6,7-dimethoxy-2-methylaminoquinazolin-4-yl)phenyl]terephthalamic acid A suspension of 2.000 kg (6.39 mol) of [4-(3-aminophenyl)-6,7-dimethoxyquinazolin-2-yl]methylamine in 71.14 kg of tetrahydrofuran was stirred in a nitrogen atmosphere while being cooled at 0° C. To the suspension was added dropwise 16.70 kg of "monomethyl terephthalate chloride/N,N-diisopropylethylamine" solution (monomethyl terephthalate chloride content: 1.40 kg, 7.03 mol) over 1 hour and 26 minutes, and the container was washed with 1.40 L of 1,2-dimethoxyethane. The mixture was stirred at 0° C. for 13 hours and 4 minutes. Under cooling at 0° C., 36.5 kg of ethyl acetate was added to the reaction mixture and then 80.1 kg of a 5% aqueous solution of sodium hydrogencarbonate was added dropwise, and the mixture was stirred at 20° C. for 1 hour and 10 minutes. Then, 37.3 kg of ethyl acetate was added into the mixture, the mixture was stirred, and the water layer was separated. The organic layer was washed with 40.0 kg of a 5% aqueous solution of sodium chloride, 40.2 kg of water, and 40.1 kg of water in this order. The organic layer was concentrated under reduced pressure at a jacket temperature of 40° C., 23.70 kg of methanol was added to the residue, and stirred for 1 hour and 1 minute while being heated to 60 to 66° C. 23.60 kg of 2-propanol was added dropwise to the suspension over 1 hour while stirring the suspension at a jacket temperature of 50° C. Then, the suspension was cooled at a cooling rate of 10° C./hour and stirred at 20° C. for 12 hours and 23 minutes. The precipitated crystals were filtered, rinsed with a mixed solution of 3.00 L of methanol and 3.00 L of 2-propanol and 6.00 L of 2-propanol in this order to give 5.52 kg of a crude product (content of the target compound: 2.57 kg, 5.44 mol) as pale yellow crystals (yield: 85.3%).

In a nitrogen atmosphere, a suspension of 5.398 kg of the crude product (content of the target compound: 2.518 kg, 5.33 mol) in 8.01 L of dimethyl sulfoxide was stirred under heating at 60 to 70° C., and the crystals were dissolved. The solution was filtered, and rinsed with 2.00 L of dimethyl sulfoxide. The filtrate was transferred into a 210 L reaction vessel having been heated at 60° C. and the container was washed with 2.01 L of dimethyl sulfoxide. To the solution, 18.9 kg of 2-propanol was added dropwise over 40 minutes, 15.02 g of crystals of the target compound was seeded, and 9.44 kg of 2-propanol was added dropwise over 57 minutes. After stirring the suspension at 60° C. for 1 hour and 30 minutes, the jacket temperature was set at 80° C. and the stirring was continued for 37 hours and 24 minutes. Then, 56.6 kg of 2-propanol was added dropwise to the suspension over 2 hours and 8 minutes, the mixture was cooled to 20° C. at a cooling rate of 10° C./hour and stirred at the same temperature for 65 hours and 50 minutes. The precipitated crystals were filtered, rinsed with a mixed solution of 534 mL of dimethyl sulfoxide and 4.81 L of 2-propanol and 8.01 L of 2-propanol in this order. The crystals were dried under reduced pressure at 50° C. to give 2.30 kg of the target product as yellow crystals (yield 90.8%).

Example 1

An ointment containing methyl N-[3-(6,7-dimethoxy-2-methylaminoquinazolin-4-yl)phenyl]terephthalamic acid anhydride (hereinafter referred to as Compound A) of Production example 25 was manufactured according to the prescription shown in Table 1. First, Compound A was dissolved by heating at 80° C. together with polyethylene glycol 400 and dl-α-tocopherol (Solution I). Meanwhile, white petrolatum, polyethylene glycol 4000, isopropyl myristate, glyceryl monostearate, stearic acid, and polyoxyethylene hydrogenated castor oil 40 were dissolved at 80° C. and mixed by stirring. Solution I was added to the ointment base, and mixed by stirring at 80° C. for 3 minutes. Then the mixture was cooled to 32° C. with stirring in order to produce an ointment containing 0.01% by weight of Compound A.

TABLE 1

| Ingredient | Amount (% by weight) |
|---|---|
| Compound A | 0.01 |
| White petrolatum | 48.9 |
| Polyethylene glycol400 | 20 |
| Isopropylmyristate | 10 |
| Polyethylene glycol4000 | 10 |
| Glycerylmonostearate | 5 |
| Stearic acid | 5 |
| Polyoxyethylene hydrogenated castor oil40 | 1 |
| dl-a-Tocopherol | 0.1 |

Example 2

An ointment containing 0.01% by weight of Compound A was manufactured according to the prescription shown in Table 2 in the same manner as in Example 1.

TABLE 2

| Ingredient | Amount (% by weight) |
|---|---|
| Compound A | 0.01 |
| White petrolatum | 50.9 |
| Polyethylene glycol400 | 20 |
| Isopropylmyristate | 10 |
| Polyethylene glycol4000 | 10 |
| Glycerylmonostearate | 8 |
| Polyoxyethylene hydrogenated castor oil60 | 1 |
| dl-a-Tocopherol | 0.1 |

Comparative Examples 1 to 5

An ointment containing 0.01% by weight of Compound A was manufactured according to the prescription shown in Table 3 in the same manner as in Example 1.

TABLE 3

| | Amount (% by weight) | | | | |
|---|---|---|---|---|---|
| Ingredient | Comp. Ex. 1 | Comp. Ex. 2 | Comp. Ex. 3 | Comp. Ex. 4 | Comp. Ex. 5 |
| Compound A | 0.01 | 0.01 | 0.01 | 0.01 | 0.01 |
| White petrolatum | 59.9 | 59.9 | 59.9 | 59.9 | 59.9 |
| Polyethylene glycol 400 | 20 | 20 | 20 | 10 | 10 |
| Isopropyl myristate | — | 5 | 10 | 10 | 10 |
| Paraffin | 5 | 5 | 5 | 5 | 5 |
| White beeswax | 5 | 5 | 5 | 10 | 5 |
| Squalane | 10 | 5 | — | — | — |
| Cetanol | — | — | — | 5 | — |
| Polyethylene glycol 4000 | — | — | — | — | 10 |
| dl-a-Tocopherol | 0.1 | 0.1 | 0.1 | 0.1 | 0.1 |

Test Example 1

The ointments of Examples 1 and 2 and Comparative examples 1 to 5 were filled in clear glass bottles and stored at room temperature for 1 week, and then the ointments were visually inspected for the presence or absence of bleeding of the liquid ingredients from the formulation (A, not bled; B slightly bled; C, bled).

Furthermore, an appropriate amount of each ointment was applied to the back of the hand immediately after production, and usability was evaluated (A, properly hard, B, slightly hard and difficult to apply; C, too hard for practical use).

The drug efficacy of each ointment was evaluated in the same manner as in Test examples 2 and 3 (A, markedly effective; B, effective; C, no effect). The results are shown in Tables 4 and 5.

TABLE 4

| | Ex. 1 | Ex. 2 |
|---|---|---|
| Bleeding | A | A |
| Usability | A | A |
| Drug efficacy | A | A |

TABLE 5

| | Comp. Ex. 1 | Comp. Ex. 2 | Comp. Ex. 3 | Comp. Ex. 4 | Comp. Ex. 5 |
|---|---|---|---|---|---|
| Bleeding | B | C | C | C | C |
| Usability | A | — | — | — | — |
| Drug efficacy | C | B | A | — | — |

—: Not tested

As a result of each of the above tests, the ointments of Examples 1 and 2 were superior in any evaluation item. Although Comparative example 1, which did not contain an absorption enhancer, was excellent in prevention of bleeding and usability, no drug efficacy was observed. Furthermore, Comparative examples 2 and 3, which contained an absorption enhancer instead of part or all of squalane in Comparative example 1, showed drug efficacy depending on the amount of the absorption enhancer mixed, but bleeding of liquid ingredients was observed. Furthermore, Comparative examples 4 and 5, which contained cetanol or polyethylene glycol 4000, also showed the bleeding.

Test Example 2 Effect in Oxazolone-Induced Dermatitis Model

An ointment containing 0.003, 0.01, or 0.03% of Compound A was produced in the same manner as in Example 1. An effect of suppressing dermatitis of this ointment was examined using the mouse model having clinical symptoms of dermatitis.

1) Breeding

As test animals, 5-week-old NC/Nga female mice (Japan Charles River Laboratories Japan, Inc.) were used. After 1 week or longer of acclimatization/preliminary breeding, only animals, wherein no abnormal changes were found in a general state, were used for the test.

2) Sensitization and Induction of Dermatitis

Sensitization was carried out by applying 10 μL of an acetone solution (Wako Pure Chemical Industries, Ltd.) that contained 0.3% 4-ethoxymethylene-2-phenyl-2-oxazolin-5-one (hereinafter abbreviated as "oxazolone": Sigma) to each of the left and right pinnas of mice.

Induction was carried out by applying 10 μL of 0.3% oxazolone to the left pinna of each mouse, twice in total, on the 5th day after sensitization and 3 days later. Dermatitis was induced, and the mice were divided into groups, such that symptoms in each group became uniform.

3) Application of Ointment

The aforementioned ointment (approximately 10 mg) was applied to the left pinna of each mouse once daily (2 hours or longer before stimulation with oxazolone on the stimulation days) for 7 consecutive days from the 1st day, when the ointment application was started.

An ointment not containing Compound A was applied as a control group.

4) Evaluation of Ointment

Each animal was observed for the condition of dermatitis once daily before application of the drug from the 1st day to the 8th day (no application on the 8th day). Symptoms were evaluated using scores according to the following criteria, the sum of scores of each item was obtained as the score of each individual mouse, and the mean score was calculated for each treatment group.

Criteria for each of erythema, abrasion and crust/erosion: 0, no symptom; 1, mild; 2, moderate; 3, severe.

5) Test Results

The results of dermatitis rated using scores are shown in FIG. 1. As a result of the above test, a dose-dependent dermatitis improving effect was observed in the groups given the ointment containing Compound A.

Test Example 3 Effect in Oxazolone-Induced Scratching Behavior Model

1) Breeding

As test animals, 5-week-old NC/Nga female mice (Japan SLC, Inc.) were used. For acclimation, the mice passed a preliminary breeding period of 7 days. After 1 week or longer of acclimatization/preliminary breeding, only animals, wherein no changes were found in a general state, were used for the test.

2) Sensitization and Induction of Dermatitis

Sensitization was carried out by applying 20 μL of an acetone solution that contained 0.5% oxazolone to each of the left and right pinnas of mice, which had passed an acclimation/preliminary breeding period.

Induction was carried out by applying 10 μL of 0.3% oxazolone to the left pinna of each mouse, 3 times in total, at the 4th day after sensitization, at 2 or 3 days after the 4th day after sensitization and at 2 or 3 days after said date.

3) Measurement of Scratching Behavior

Scratching behavior of mice was automatically measured using a pruritus measuring device (Micro Act Device: NeuroScience, Inc.). Mice were anesthetized with diethyl ether (Wako Pure Chemical Industries, Ltd.), and a magnet piece (diameter, 1 mm; length, 3 mm: NeuroScience, Inc.) was subcutaneously inserted into the left hind leg of each mouse by the day before measurement at latest. Oxazolone was applied to induce scratching behavior, then the mice were transferred into a chamber (diameter, 11 cm; height, 18 cm) around which a coil is wound, and electric current induced by the movement of the magnet inserted into the leg of the mouse was measured for a certain period of time. A characteristic wave form that reflects such scratching behavior was detected by the pruritus measuring device, and the appearance frequency of the detected wave form was counted as a number of scratching behaviors.

4) Administration of Ointment

The aforementioned ointment (approximately 10 mg) was applied to the left pinna at 4 hours before oxazolone stimulation. The following five test groups were determined: (1) normal group—an ointment not containing Compound A application group in which dermatitis was not induced; (2) control group—an ointment not containing Compound A application group; (3) an ointment containing 0.003% Compound A application group; (4) an ointment containing 0.01% Compound A application group; and (5) an ointment containing 0.03% Compound A application group. The mice were divided into groups, such that the number of scratching behaviors in each group became uniform based on the number of scratching behaviors obtained during the 2nd induction scratching.

5) Evaluation of Ointments

Evaluation was carried out using the number of scratching behaviors induced by the 3rd application of oxazolone (acetone was applied to the normal group) as an indicator. The number of scratching behaviors was measured at 2 hours after application of oxazolone.

6) Test Results

Figure 2:
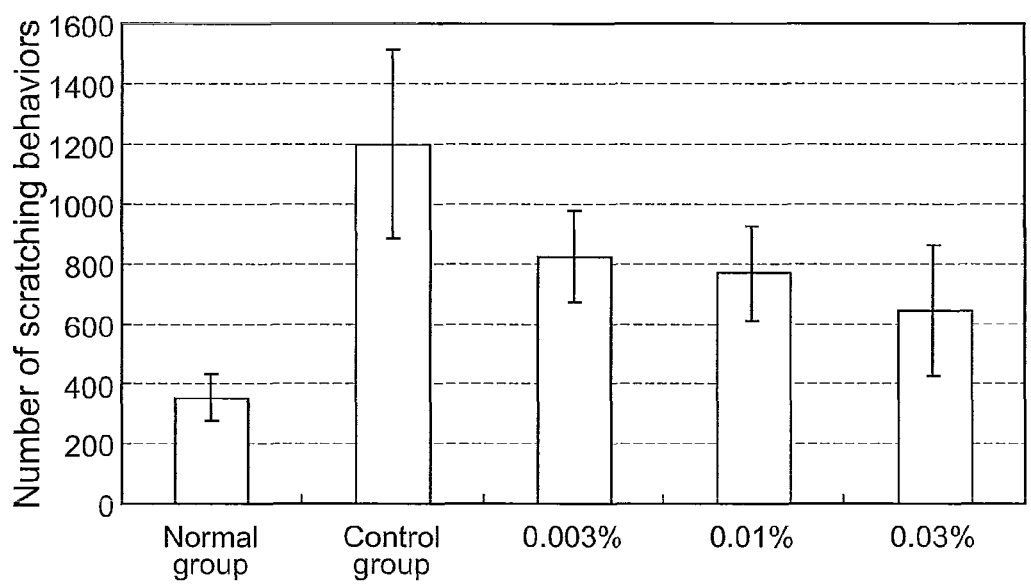
FIG. 2 shows that scratching behaviors are suppressed by the ointment of the present invention.

The results of the number of scratching behaviors are shown in FIG. 2. From these results, it was found that the ointments of the present invention suppress scratching behavior and also suppress deterioration in cutaneous symptoms caused by such scratching behavior, thereby having an excellent anti-pruritic effect.

Examples 3 to 5

An ointment containing 0.01% by weight of Compound A was manufactured according to the prescription shown in Table 6 in the same manner as in Example 1. Then, the ointments of Examples 3 to 5 were evaluated in the same manner as in Test example 1. The results are shown in Table 6. The ointments of Examples 3 to 5 were superior in the evaluation items of bleeding and usability.

TABLE 6

| | Amount (% by weight) | | |
|---|---|---|---|
| Ingredient | Example 3 | Example 4 | Example 5 |
| Compound A | 0.01 | 0.01 | 0.01 |
| White petrolatum | 55 | 60 | 50 |
| Polyethylene glycol400 | 20 | 10 | 20 |
| Isopropylmyristate | 5 | 10 | 10 |
| Polyethylene glycol4000 | 10 | 10 | 10 |
| Glycerylmonostearate | 10 | 5 | 10 |
| Stearic acid | — | 5 | — |
| dl-a-Tocopherol | 0.1 | 0.1 | 0.1 |
| Evaluation item | | | |
| Bleeding | A | A | A |
| Usability | A | A | A |

Examples 6 to 9

An ointment containing 0.01% by weight of Compound A was manufactured according to the prescription shown in Table 7 in the same manner as in Example 1. Water was added together with Solution I. Then, the ointments of Examples 6 to 9 were evaluated in the same manner as in Test example 1. The results are shown in Table 6. The ointments of Examples 6 to 9 were superior in the evaluation items of bleeding and usability.

TABLE 7

| | Amount (% by weight) | | | |
|---|---|---|---|---|
| Ingredient | Ex. 6 | Ex. 7 | Ex. 8 | Ex. 9 |
| Compound A | 0.01 | 0.01 | 0.01 | 0.01 |
| White petrolatum | 50.9 | 50.4 | 49.9 | 48.9 |
| Water | 0 | 0.5 | 1 | 2 |
| Polyethylene glycol400 | 20 | 20 | 20 | 20 |
| Isopropylmyristate | 10 | 10 | 10 | 10 |
| Polyethylene glycol4000 | 10 | 10 | 10 | 10 |
| Glycerylmonostearate | 8 | 8 | 8 | 8 |
| Polyoxyethylene hydrogenated castor oil60 | 1 | 1 | 1 | 1 |
| dl-a-Tocopherol | 0.1 | 0.1 | 0.1 | 0.1 |
| Evaluation item | | | | |
| Bleeding | A | A | A | A |
| Usability | A | A | A | A |

Test Example 4 Evaluation of Stability of Ointments

The ointments of Examples 6 to 9 were filled in a 20-mL light-resistant glass bottle and stored at 5° C. or 40° C. for a predetermined period, and the amount of impurities was measured by HPLC to evaluate the stability of ointments. The results are shown in Table 8 (numerical values are the values (%) obtained by dividing the main impurities peak area by the active ingredient peak area, and ND indicates that impurities could not be detected). Impurities were detected in the ointment of Example 6, to which water was not added and which was stored at 5° C. for 2 weeks, but no impurities were detected in the ointment of Example 9, to which 2% water was added and which was stored at 40° C. for 1 month.

TABLE 8

| | | | At 2 weeks | | At 1 month | |
|---|---|---|---|---|---|---|
| Example | Amount of water | Initial | 5° C. | 40° C. | 5° C. | 40° C. |
| 6 | 0% | ND | 0.58 | 1.49 | 1.33 | 2.01 |
| 7 | 0.5% | ND | ND | 0.62 | 0.46 | 1.05 |
| 8 | 1% | ND | ND | ND | ND | 0.76 |
| 9 | 2% | ND | ND | ND | ND | ND |

The conditions of HPLC were as follows.

Detector: Ultraviolet absorption meter (measurement wavelength 249 nm)

Column: Stainless tube (inner diameter, 4.6 mm; length, 25 cm) filled with 5 μm octadecylsilylated silica gel for liquid chromatography Column temperature: Constant temperature around 45° C.

Mobile phase: Mixed solution of water/acetonitrile/70% perchloric acid (120:80:1)

Flow rate: Approximately 1.5 mL/min

INDUSTRIAL APPLICABILITY

The topical formulation of the present invention can be used as a therapeutic agent for allergic dermatitis such as atopic dermatitis, contact dermatitis and the like.

The invention claimed is:

1. A topical formulation, comprising a compound represented by the formula (I), or salt thereof:

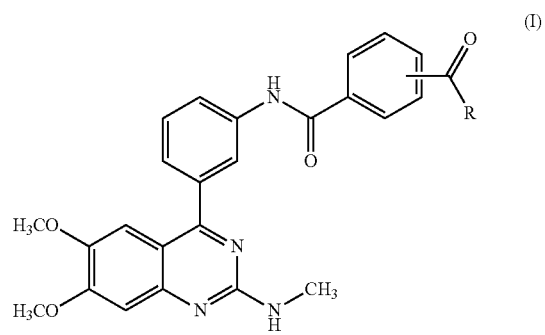

wherein R represents hydroxyl, $C_{1-6}$ alkoxy optionally substituted with $C_{1-6}$ alkoxy, or amino optionally substituted with $C_{1-6}$ alkyl,
  one or more solvents selected from the group consisting of polyethylene glycol having a molecular weight of 200 to 600, dipropylene glycol, benzyl alcohol, polyoxyethylene sorbitan fatty acid ester, diethylene glycol monoethyl ether, propylene glycol, polyoxyethylene oleyl ether, polyoxyethylene octyl phenyl ether, polyoxyethylene lauryl ether, polyoxyethylene castor oil, and oleic acid,
  one or more bases selected from the group consisting of petrolatum, paraffin, liquid paraffin, microcrystalline wax, carunauba wax, and white beeswax
  one or more absorption enhancers selected from the group consisting of isopropyl myristate, ethyl myristate, octyldodecyl myristate, isopropyl palmitate, isostearyl palmitate, isopropyl isostearate, butyl stearate, ethyl oleate, decyl oleate, diisopropyl sebacate, diethyl sebacate, diisopropyl adipate, diethyl adipate, and diethyl phthalate,
  two or more bleeding preventing agents selected from the group consisting of polyethylene glycol having a molecular weight of 1000 to 50000, polyoxyethylene hydrogenated castor oil, stearic acid, oleic acid, sorbitan monostearate, sorbitan monooleate, sorbitan sesquioleate, sorbitan trioleate, and glycerol esters of fatty acids, and
  water.

2. The topical formulation according to claim 1, wherein the compound represented by the formula (I) is methyl N-[3-(6,7-dimethoxy-2-methylaminoquinazolin-4-yl)phenyl] terephthalamic acid.

3. The topical formulation according to claim 1, wherein the glycerol esters of fatty acids is one or more types selected from the group consisting of glyceryl monostearate, diglyceryl isostearate, and hexaglyceryl polyricinoleate.

4. The topical formulation according to claim 1, wherein the bleeding preventing agents are polyethylene glycol having a molecular weight of 1000 to 50000 and glycerol esters of fatty acids.

5. The topical formulation according to claim 4, wherein the bleeding preventing agent is glyceryl monostearate.

6. The topical formulation according to claim 1, wherein the topical formulation comprises 10 to 30% by weight of a solvent and 5 to 20% by weight of an absorption enhancer, and the sum of the solvent and absorption enhancer is 20 to 40% by weight based on the total preparation amount, respectively.

7. A method for preventing bleeding of liquid ingredients, comprising mixing polyethylene glycol having a molecular weight of 1000 to 50000 and glycerol esters of fatty acids in a topical formulation according to claim 1.

* * * * *